US008016784B1

(12) United States Patent
Hayzelden et al.

(10) Patent No.: US 8,016,784 B1
(45) Date of Patent: Sep. 13, 2011

(54) DEFLECTABLE CATHETER ASSEMBLY HAVING COMPRESSION COMPENSATION MECHANISM

(75) Inventors: Robert Hayzelden, Canyon Lake, CA (US); William E. Webler, Escondido, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1675 days.

(21) Appl. No.: 10/740,725

(22) Filed: Dec. 18, 2003

Related U.S. Application Data

(63) Continuation-in-part of application No. 10/676,616, filed on Sep. 30, 2003.

(51) Int. Cl.
*A61M 31/00* (2006.01)

(52) U.S. Cl. .................. 604/93.01; 604/95.03; 604/104

(58) Field of Classification Search .... 604/95.01–95.05, 604/523–532, 104–109
See application file for complete search history.

(56) References Cited

U.S. PATENT DOCUMENTS 3,177,543 A 4/1965 Fountain
3,716,058 A 2/1973 Tanner, Jr.
4,128,100 A 12/1978 Wendorff
4,719,924 A 1/1988 Crittenden et al.
4,781,186 A 11/1988 Simpson et al.
4,817,250 A 4/1989 Kurosaki
4,830,023 A 5/1989 de Toledo et al.
4,920,980 A 5/1990 Jackowski
4,927,421 A 5/1990 Goble et al.
4,994,067 A 2/1991 Summers
5,040,548 A 8/1991 Yock
5,061,273 A 10/1991 Yock
5,100,418 A 3/1992 Yoon et al.
5,100,421 A 3/1992 Christoudias
5,102,421 A 4/1992 Anspach, Jr.
5,116,337 A 5/1992 Johnson
5,129,902 A 7/1992 Goble et al.
5,141,520 A 8/1992 Goble et al.
5,171,233 A 12/1992 Amplatz et al.

(Continued)

FOREIGN PATENT DOCUMENTS

DE 10161543 6/2003

(Continued)

OTHER PUBLICATIONS

Messas, et al., "Chordal Cutting a New Therapeutic Approach for Ischmic Mitral Regurgitaion," 2001, American Heart Association Inc., pp. 1958-1963.

(Continued)

*Primary Examiner* — Theodore J Stigell
*Assistant Examiner* — Phillip Gray
(74) *Attorney, Agent, or Firm* — Blakely Sokoloff Taylor & Zafman LLP

(57) ABSTRACT

A deflectable catheter assembly having a compression compensation mechanism is disclosed. The deflectable catheter assembly comprises a catheter shaft having a catheter proximal section and a catheter distal section. A therapeutic tool is disposed within the catheter shaft. A compression compensation mechanism is coupled to the therapeutic tool to compensate for a length change in the catheter shaft such as when the catheter shaft is deflected. The compression compensation mechanism includes a spring moveably disposed between a distal stop and a proximal stop that are attached to the therapeutic tool. A deployment slide is moveably disposed proximate to the spring and between the distal stop and the proximal stop. A catheter handle configured to house the compression compensation mechanism is coupled to the catheter shaft.

46 Claims, 12 Drawing Sheets

U.S. PATENT DOCUMENTS

| | | | |
|---|---|---|---|
| 5,201,598 | A | 4/1993 | Tehan |
| 5,234,443 | A | 8/1993 | Phan et al. |
| 5,242,456 | A | 9/1993 | Nash et al. |
| 5,246,441 | A | 9/1993 | Ross et al. |
| 5,350,395 | A | 9/1994 | Yock |
| 5,358,479 | A | 10/1994 | Wilson |
| 5,370,662 | A | 12/1994 | Stone et al. |
| 5,374,275 | A | 12/1994 | Bradley et al. |
| 5,383,260 | A | 1/1995 | Deschenes et al. |
| 5,431,673 | A | 7/1995 | Summers et al. |
| 5,441,483 | A | 8/1995 | Avitall |
| 5,441,499 | A | 8/1995 | Fritzsch |
| 5,451,233 | A | 9/1995 | Yock |
| 5,456,667 | A | 10/1995 | Ham et al. |
| 5,487,757 | A | 1/1996 | Truckai et al. |
| 5,495,974 | A | 3/1996 | Deschenes et al. |
| 5,518,162 | A | 5/1996 | Deschenes et al. |
| 5,531,686 | A | 7/1996 | Lundquist et al. |
| 5,554,184 | A | 9/1996 | Machiraju |
| 5,569,277 | A | 10/1996 | Evans et al. |
| 5,588,188 | A | 12/1996 | Jermyn, Jr. |
| 5,609,598 | A | 3/1997 | Laufer et al. |
| 5,626,613 | A | 5/1997 | Schmieding |
| 5,632,754 | A | 5/1997 | Farley et al. |
| 5,681,280 | A | 10/1997 | Rusk et al. |
| 5,728,129 | A | 3/1998 | Summers |
| 5,810,882 | A | 9/1998 | Bolduc et al. |
| 5,824,008 | A | 10/1998 | Bolduc et al. |
| 5,865,800 | A | 2/1999 | Mirarchi et al. |
| 5,868,767 | A | 2/1999 | Farley et al. |
| 5,954,731 | A | 9/1999 | Yoon |
| 5,961,440 | A | 10/1999 | Schweich, Jr. et al. |
| 5,964,772 | A | 10/1999 | Bolduc et al. |
| 5,972,022 | A | 10/1999 | Huxel |
| 6,001,095 | A | 12/1999 | de la Rama et al. |
| 6,001,104 | A | 12/1999 | Benderev et al. |
| 6,001,127 | A | 12/1999 | Schoon et al. |
| 6,004,332 | A | 12/1999 | Yoon et al. |
| 6,017,358 | A | 1/2000 | Yoon et al. |
| 6,027,514 | A | 2/2000 | Stine et al. |
| 6,036,715 | A | 3/2000 | Yock |
| 6,045,497 | A | 4/2000 | Schweich, Jr. et al. |
| 6,050,936 | A | 4/2000 | Schweich, Jr. et al. |
| 6,051,008 | A | 4/2000 | Saadat et al. |
| 6,059,715 | A | 5/2000 | Schweich, Jr. et al. |
| 6,077,214 | A | 6/2000 | Mortier et al. |
| 6,093,199 | A | 7/2000 | Brown et al. |
| 6,102,887 | A | 8/2000 | Altman |
| 6,110,100 | A | 8/2000 | Talpade |
| 6,113,609 | A | 9/2000 | Adams |
| 6,120,520 | A | 9/2000 | Saadat et al. |
| 6,123,699 | A | 9/2000 | Webster, Jr. |
| 6,149,669 | A | 11/2000 | Li |
| 6,161,543 | A | 12/2000 | Cox et al. |
| 6,162,168 | A | 12/2000 | Schweich, Jr. et al. |
| 6,165,119 | A | 12/2000 | Schweich, Jr. et al. |
| 6,165,120 | A | 12/2000 | Schweich, Jr. et al. |
| 6,165,164 | A | 12/2000 | Hill et al. |
| 6,165,183 | A | 12/2000 | Kuehn et al. |
| 6,165,197 | A | 12/2000 | Yock |
| 6,174,323 | B1 | 1/2001 | Biggs et al. |
| 6,176,240 | B1 | 1/2001 | Nikolchev et al. |
| 6,178,346 | B1 | 1/2001 | Amundson et al. |
| 6,182,664 | B1 | 2/2001 | Cosgrove |
| 6,183,411 | B1 | 2/2001 | Mortier et al. |
| 6,187,040 | B1 | 2/2001 | Wright |
| 6,190,401 | B1 | 2/2001 | Green et al. |
| 6,210,407 | B1 | 4/2001 | Webster |
| 6,210,432 | B1 | 4/2001 | Solem et al. |
| 6,231,561 | B1 | 5/2001 | Frazier et al. |
| 6,231,587 | B1 | 5/2001 | Makower |
| 6,254,568 | B1 | 7/2001 | Ponzi |
| 6,254,598 | B1 | 7/2001 | Edwards et al. |
| 6,260,552 | B1 | 7/2001 | Mortier et al. |
| 6,261,222 | B1 | 7/2001 | Schweich, Jr. et al. |
| 6,264,602 | B1 | 7/2001 | Mortier et al. |
| 6,269,819 | B1 | 8/2001 | Oz et al. |
| 6,270,526 | B1 | 8/2001 | Cox |
| 6,299,622 | B1 | 10/2001 | Snow et al. |
| 6,312,447 | B1 | 11/2001 | Grimes |
| 6,325,823 | B1 | 12/2001 | Horzewski et al. |
| 6,355,030 | B1 | 3/2002 | Aldrich et al. |
| 6,371,978 | B1 | 4/2002 | Wilson |
| 6,374,476 | B1 | 4/2002 | Ponzi et al. |
| 6,402,780 | B2 | 6/2002 | Williamson, IV et al. |
| 6,402,781 | B1 | 6/2002 | Langberg et al. |
| 6,419,696 | B1 | 7/2002 | Ortiz et al. |
| 6,461,366 | B1 | 10/2002 | Seguin |
| 6,482,224 | B1 | 11/2002 | Michler et al. |
| 6,488,689 | B1 | 12/2002 | Kaplan et al. |
| 6,493,575 | B1 | 12/2002 | Kesten et al. |
| 6,497,707 | B1 | 12/2002 | Bowman et al. |
| 6,500,167 | B1 | 12/2002 | Webster, Jr. |
| 6,517,553 | B2 | 2/2003 | Klein et al. |
| 6,537,198 | B1 | 3/2003 | Vidlund et al. |
| 6,537,314 | B2 | 3/2003 | Langberg et al. |
| 6,551,271 | B2 | 4/2003 | Nguyen |
| 6,554,794 | B1 | 4/2003 | Mueller et al. |
| 6,554,852 | B1 | 4/2003 | Oberlander |
| 6,585,718 | B2 | 7/2003 | Hayzelden et al. |
| 6,599,311 | B1 | 7/2003 | Biggs et al. |
| 6,605,086 | B2 | 8/2003 | Hayzelden et al. |
| 6,610,058 | B2 | 8/2003 | Flores |
| 6,619,291 | B2 | 9/2003 | Hlavka et al. |
| 6,626,899 | B2 | 9/2003 | Houser et al. |
| 6,626,930 | B1 | 9/2003 | Allen et al. |
| 6,629,534 | B1 | 10/2003 | Dell et al. |
| 6,638,286 | B1 | 10/2003 | Burbank et al. |
| 6,638,289 | B1 | 10/2003 | Johnson et al. |
| 6,648,903 | B1 | 11/2003 | Pierson, III |
| 6,656,221 | B2 | 12/2003 | Taylor et al. |
| 6,676,702 | B2 | 1/2004 | Mathis |
| 6,706,065 | B2 | 3/2004 | Langberg et al. |
| 6,709,442 | B2 | 3/2004 | Miller et al. |
| 6,709,456 | B2 | 3/2004 | Langberg et al. |
| 6,712,804 | B2 | 3/2004 | Roue et al. |
| 6,718,985 | B2 | 4/2004 | Hlavka et al. |
| 6,719,767 | B1 | 4/2004 | Kimblad |
| 6,723,038 | B1 | 4/2004 | Schroeder et al. |
| 6,746,472 | B2 | 6/2004 | Frazier et al. |
| 6,761,734 | B2 | 7/2004 | Suhr |
| 6,764,510 | B2 | 7/2004 | Vidlund et al. |
| 6,770,070 | B1 | 8/2004 | Balbierz |
| 6,790,231 | B2 | 9/2004 | Liddicoat et al. |
| 6,800,090 | B2 | 10/2004 | Alferness et al. |
| 6,810,882 | B2 | 11/2004 | Langberg et al. |
| 6,824,562 | B2 | 11/2004 | Mathis et al. |
| 6,852,124 | B2 | 2/2005 | Cox et al. |
| 6,890,353 | B2 | 5/2005 | Cohn et al. |
| 6,905,476 | B2 * | 6/2005 | Ponzi ......................... 604/95.01 |
| 6,951,549 | B1 | 10/2005 | Beyerlein |
| 6,960,229 | B2 | 11/2005 | Mathis et al. |
| 6,964,683 | B2 | 11/2005 | Kowalsky et al. |
| 6,966,926 | B2 | 11/2005 | Mathis |
| 6,989,028 | B2 | 1/2006 | Lashinski et al. |
| 6,997,951 | B2 | 2/2006 | Solem et al. |
| 7,087,064 | B1 | 8/2006 | Hyde |
| 7,104,999 | B2 | 9/2006 | Overaker |
| 7,247,149 | B2 | 7/2007 | Beyerlein |
| 7,364,567 | B2 | 4/2008 | Beyerlein |
| 2001/0003986 | A1 | 6/2001 | Cosgrove |
| 2001/0005787 | A1 | 6/2001 | Oz et al. |
| 2001/0018611 | A1 | 8/2001 | Solem et al. |
| 2001/0027322 | A1 | 10/2001 | Bowman |
| 2001/0044568 | A1 | 11/2001 | Langberg et al. |
| 2002/0010483 | A1 | 1/2002 | Folmer et al. |
| 2002/0010486 | A1 | 1/2002 | Hirt |
| 2002/0013571 | A1 | 1/2002 | Goldfarb et al. |
| 2002/0016628 | A1 | 2/2002 | Langberg et al. |
| 2002/0026216 | A1 | 2/2002 | Grimes |
| 2002/0035361 | A1 | 3/2002 | Houser et al. |
| 2002/0042651 | A1 | 4/2002 | Liddicoat et al. |
| 2002/0077647 | A1 | 6/2002 | Snow et al. |
| 2002/0087169 | A1 | 7/2002 | Brock et al. |
| 2002/0087173 | A1 | 7/2002 | Alferness et al. |
| 2002/0103492 | A1 | 8/2002 | Kaplan et al. |
| 2002/0103532 | A1 | 8/2002 | Langberg et al. |

| | | | |
|---|---|---|---|
| 2002/0103553 | A1 | 8/2002 | Phillips |
| 2002/0111637 | A1 | 8/2002 | Kaplan et al. |
| 2002/0161330 | A1 | 10/2002 | Nguyen |
| 2002/0165484 | A1 | 11/2002 | Bowe et al. |
| 2002/0165533 | A1 | 11/2002 | Flores |
| 2002/0165534 | A1 | 11/2002 | Hayzelden et al. |
| 2002/0169502 | A1 | 11/2002 | Mathis |
| 2002/0169504 | A1 | 11/2002 | Alferness et al. |
| 2002/0183836 | A1 | 12/2002 | Liddicoat et al. |
| 2002/0183837 | A1 | 12/2002 | Streeter et al. |
| 2002/0183841 | A1 | 12/2002 | Cohn et al. |
| 2002/0188170 | A1 | 12/2002 | Santamore et al. |
| 2003/0050598 | A1 | 3/2003 | Hayzelden et al. |
| 2003/0069593 | A1 | 4/2003 | Tremulis et al. |
| 2003/0078465 | A1 | 4/2003 | Pai et al. |
| 2003/0093071 | A1 | 5/2003 | Hauck et al. |
| 2003/0105520 | A1 | 6/2003 | Alferness et al. |
| 2003/0120340 | A1 | 6/2003 | Liska et al. |
| 2003/0120341 | A1 | 6/2003 | Shennib et al. |
| 2003/0130731 | A1 | 7/2003 | Vidlund et al. |
| 2003/0144732 | A1 | 7/2003 | Cosgrove et al. |
| 2003/0167071 | A1 | 9/2003 | Martin et al. |
| 2003/0171776 | A1 | 9/2003 | Adams et al. |
| 2003/0212453 | A1 | 11/2003 | Mathis et al. |
| 2003/0216764 | A1 | 11/2003 | Tu et al. |
| 2004/0010231 | A1 | 1/2004 | Leonhardt et al. |
| 2004/0044350 | A1 | 3/2004 | Martin et al. |
| 2004/0044365 | A1 | 3/2004 | Bachman |
| 2004/0049207 | A1 | 3/2004 | Goldfarb et al. |
| 2004/0059351 | A1 | 3/2004 | Eigler et al. |
| 2004/0098092 | A1 | 5/2004 | Butaric et al. |
| 2004/0138683 | A1 | 7/2004 | Shelton et al. |
| 2004/0138744 | A1 | 7/2004 | Lashinski et al. |
| 2004/0153147 | A1 | 8/2004 | Mathis |
| 2005/0267571 | A1 | 12/2005 | Spence et al. |
| 2006/0041306 | A1 | 2/2006 | Vidlund et al. |
| 2006/0095025 | A1 | 5/2006 | Levine et al. |

FOREIGN PATENT DOCUMENTS

| | | | |
|---|---|---|---|
| DE | 10161543 | A1 | 6/2003 |
| EP | 0377269 | A1 | 7/1990 |
| EP | 0980693 | | 2/2000 |
| JP | 5329216 | | 12/1993 |
| WO | WO-9111213 | | 8/1991 |
| WO | WO-9503843 | | 2/1995 |
| WO | WO 98/29041 | A1 | 7/1998 |
| WO | WO 99/00059 | | 1/1999 |
| WO | WO 99/13777 | | 3/1999 |
| WO | WO 99/30647 | A1 | 6/1999 |
| WO | WO 99/44534 | A1 | 9/1999 |
| WO | WO 00/03759 | | 1/2000 |
| WO | WO 00/06026 | A2 | 2/2000 |
| WO | WO 00/06027 | A2 | 2/2000 |
| WO | WO 00/06028 | A1 | 2/2000 |
| WO | WO-0009185 | | 2/2000 |
| WO | WO 00/16700 | A1 | 3/2000 |
| WO | WO 00/60995 | | 10/2000 |
| WO | WO 01/00111 | A1 | 1/2001 |
| WO | WO 01/00114 | A1 | 1/2001 |
| WO | WO 01/26557 | A1 | 4/2001 |
| WO | WO 01/28432 | A1 | 4/2001 |
| WO | WO 01/28455 | A1 | 4/2001 |
| WO | WO 01/49213 | A2 | 7/2001 |
| WO | WO 01/49213 | A3 | 7/2001 |
| WO | WO 01/54618 | A1 | 8/2001 |
| WO | WO 01/89440 | A2 | 11/2001 |
| WO | WO 02/00099 | A2 | 1/2002 |
| WO | WO 02/01999 | A2 | 1/2002 |
| WO | WO 02/34167 | A2 | 5/2002 |
| WO | WO 02/39925 | A2 | 5/2002 |
| WO | WO 02/053206 | A2 | 7/2002 |
| WO | WO 02/060352 | | 8/2002 |
| WO | WO 02/062263 | A2 | 8/2002 |
| WO | WO 02/062270 | A1 | 8/2002 |
| WO | WO 02/062408 | A2 | 8/2002 |
| WO | WO 03/049619 | A2 | 6/2003 |
| WO | WO 03/073913 | A2 | 9/2003 |
| WO | WO 2004/012789 | A2 | 2/2004 |
| WO | WO 2004/014282 | A2 | 2/2004 |

OTHER PUBLICATIONS

Bonow, Robert O., et al., "Guidelines for the Management of Patients with Valvular Health Disease," Report of American College of Cardiology/American Heart Assoc. Task Force on Practice Guidelnes (Committee on Mangement of Pateints with Valvular Heart Disease), American College of Cardiology and American Heart Assoc., Inc., 1998, pp. 1949-1984.

PCT Invitation to Pay Additional fees for PCT International Appln. No. US03/36633, mailed May 19, 2004 (5 pages).

PCT Report for PCT International Patent Application PCT/US2004/031403, mailed Jun. 15, 2005. 5 pgs.

PCT International Preliminary Report on Patentability and Written Opinion for PCT Appln. No. US2004/031403, mailed Apr. 13, 2006 (8 pages).

PCT International Search Report and Written Opinion of the International Searching Authority for PCT Appln No. US2004/031403, mailed May 18, 2005 (14 pages).

PCT International Search Report for PCT Appln No. US2004/031403, mailed Feb. 15, 2005 (5 pages).

"Non-Final Office Action", U.S. Appl. No. 10/740,360, (Aug. 19, 2008), 8 pages.

Abbott Cardiovascular Systems, Final Office Action dated Apr. 15, 2009 for U.S. Appl. No. 10/676,616.

Abbott Cardiovascular Systems, Office Action dated Jan. 25, 2010 for Japanese Patent Application No. 2006-533979.

Abbott Cardiovascular Systems, Non-final Office Action mailed Aug. 13, 2010 for U.S. Appl. No. 10/676,616, 15 pages.

Abbott Cardiovascular Systems Inc., Final office action mailed Dec. 6, 2010 for U.S. Appl. No. 10/676,616 (13 pages).

Abbott Cardiovascular Systems, European search report dated Feb. 18, 2011 for EP Application No. 10185686.2.

Abbott Cardiovascular Systems, Office Action dated Feb. 7, 2011 for Japanese Patent Application No. 2006-533979.

* cited by examiner

DEFLECTABLE CATHETER ASSEMBLY HAVING COMPRESSION COMPENSATION MECHANISM

RELATED APPLICATION

This application is a continuation in part of application Ser. No. 10/676,616, filed Sep. 30, 2003 entitled "Deflectable catheter assembly and method of making same," which is hereby incorporated by reference in its entirety.

BACKGROUND

1. Field

Many aspects of this disclosure relate to a deflectable catheter assembly having a compression compensation mechanism. The catheter assembly of an exemplary embodiment includes a deflectable distal section, a non-deflectable section, a proximal catheter handle, and a tool (e.g., a needle, a therapeutic device, and a diagnostic device), and a compression compensation mechanism coupled to the tool.

2. Discussion of Related Art

Steerable catheters have been commonly used in applications such as mapping (e.g., cardiac mapping), drug delivery (e.g., intramyocardial drug delivery), and ablation, (e.g., arrhythmia ablation).

A steerable catheter has a deflectable flexible distal section and a stiffer proximal torqueable shaft. The steerable function is accomplished by three modes of actions: 1) translational catheter movement along the shaft direction, 2) deflection of the distal deflectable section, and 3) turning of the catheter shaft to direct the deflection toward the target therapy site. A tendon wire is included to control the deflection of the distal section. This tendon wire is located inside of a sheath running along and within the catheter shaft with its distal end attached near the distal tip of the catheter. A pulling mechanism is included within the proximal catheter handle, which is coupled to the proximal end of the catheter shaft. The pulling mechanism controls the tendon wire to deflect the distal section of the catheter shaft. Radially, the tendon wire is located off-center of the catheter shaft center to create a moment toward the intended deflection side in the catheter distal deflectable section. When the tendon wire is pulled, the catheter deflects toward the radial direction to which the tendon wire is located. The deflection section is typically made to be much more flexible than the rest of the catheter shaft. When the tendon wire is pulled in tension, the catheter shaft wants to "curl up." The distal section is the most flexible section of the catheter shaft and thus it deflects when the tendon wire is pulled. To direct the deflected section toward the target site, an operator turns the catheter shaft on the proximal end. The deflection section responds to the torque in a fashion that is governed by the way the catheter is constructed.

Depending on the therapeutic use of the catheter, a therapeutic tool, such as a needle, may run in parallel to the tendon wire within the catheter shaft.

Deflectable catheters have been in common use in medical practice for many years. The catheters are used to probe locations inside a body lumen that are otherwise unreachable without surgery. A catheter is inserted into a major vein or artery, or other body lumen that is near the body surface, possibly with the aid of an introducer entering the body lumen and a guide catheter previously inserted.

The catheter is then guided to the area of concern by inserting the catheter further into the body lumen. As medical knowledge increases, catheterizations have become more complicated and exacting. In many situations the ability to control the position and orientation of the catheter tip may largely determine the usefulness of the catheter.

In a steerable catheter, deflecting the distal tip of the catheter to a bent shape causes the outer catheter body or shaft to undergo some compression and some shortening in length. Devices internal to the catheter body (e.g., a needle assembly) and not connected directly to the catheter body do not change in length, or at least do not change in length as much, when the distal tip of the catheter is deflected. The internal devices thus become longer relative to the outer catheter body. This change in relative length can affect the deployment of the internal devices. For instances, a needle may extend longer than anticipated due to the compression. The needle is thus not in the expected position which may require the operator/physician to have to make further adjustment.

SUMMARY

There is a need for catheter assemblies that can compensate for the compression of the catheter shaft for example, as caused by the deflection of the catheter shaft.

Embodiments are pertained to a catheter assembly having a compression compensation mechanism. The catheter assembly comprises a catheter shaft having a catheter proximal section and a catheter distal section. A therapeutic tool is disposed within the catheter shaft. A compression compensation mechanism is coupled to a therapeutic tool proximal end to compensate for a length change in the catheter shaft for example, as the catheter shaft is deflected. The compression compensation mechanism includes a spring moveably disposed between a distal stop and a proximal stop. The distal stop and the proximal stop are fixedly and attached to the therapeutic tool. A therapeutic tool deployment slide is disposed proximate to the spring and between the distal stop and the proximal stop. The spring is mechanically constrained between the distal stop and the deployment slide. The therapeutic tool can be a needle. A catheter handle configured to house the compression compensation mechanism is coupled to the catheter shaft.

In one embodiment, the therapeutic tool includes a stop mechanism that controls the extension and retraction distance of the therapeutic tool out of the catheter shaft.

In another embodiment, the compression compensation mechanism includes two springs disposed between the distal stop and the proximal stop wherein a first spring is mechanically constrained between the distal stop and the deployment slide and a second spring is mechanically constrained between the deployment slide and the proximal stop.

In another embodiment, the catheter assembly is a deflectable catheter assembly wherein a tendon configured to deflect the catheter distal section is disposed within the catheter shaft.

These and other features and advantages of embodiments of the present invention will be more readily apparent from the detailed description of the embodiments, set forth below, taken in conjunction with the accompanying drawings.

BRIEF DESCRIPTION OF THE DRAWINGS

The present invention is illustrated by way of example and not limitation in the figures of the accompanying drawings, in which like references indicate similar elements and in which.

The features of the described embodiments are specifically set forth in the appended claims. The embodiments are best understood by referring to the following description and accompanying drawings, in which similar parts are identified by like reference numerals.

DETAILED DESCRIPTION

Many aspects of this disclosure relate to a catheter assembly having a compression compensation mechanism. Methods of making and using an exemplary catheter assembly are also disclosed. One aspect of this disclosure relates to a needle injection catheter assembly, for delivery of a biologic agent into the wall tissue of the heart, which includes an injection needle that includes a compression compensation mechanism, a catheter shaft that includes a deflectable distal section, and a torque-transmitting shaft, and a catheter handle. As the deflectable catheter assembly deflects, the catheter shaft included in the catheter assembly compresses. As the catheter shaft compresses, the internal devices such as a needle extends out of the shaft more than expected causing difficult positioning of the needle. The compression compensation mechanism that is coupled to the needle to compensate for the compression of the catheter shaft. It is to be understood that the compression compensation mechanism can be incorporated into various types of catheter assemblies (not just deflectable catheter assemblies) that may experience catheter shaft compression or length changes.

In the following description, for purposes of explanation, numerous specific details are set forth in order to provide a thorough understanding of the exemplary embodiments of the present invention. It will be evident, however, to one skilled in the art, that these embodiments may be practiced without these specific details. In other instances, specific structures and methods have not been described so as not to obscure the present invention. The following description and drawings are illustrative of the invention and are not to be construed as limiting the invention.

Figure 1:
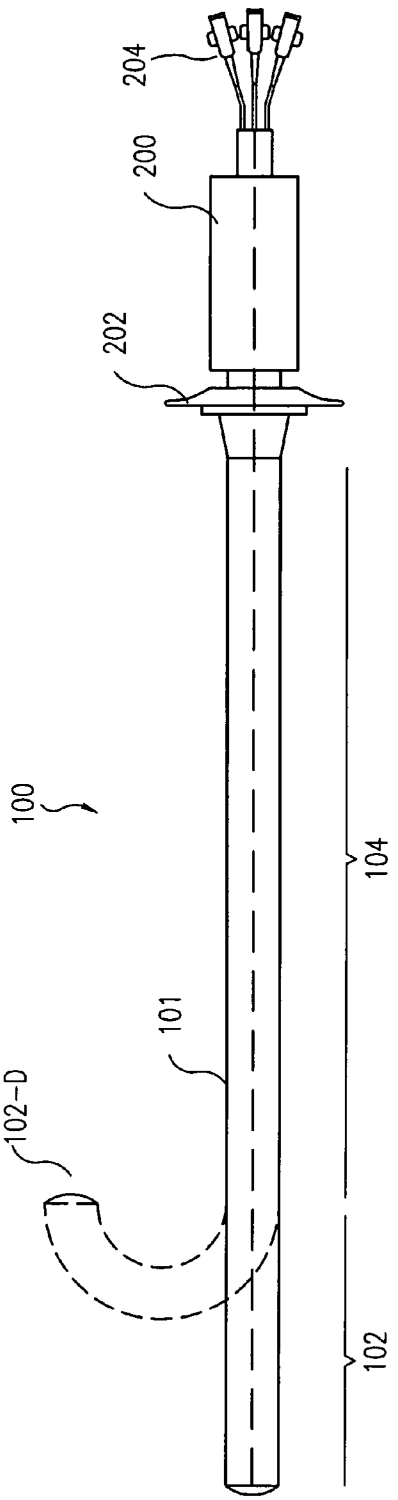
FIG. 1 illustrates an exemplary embodiment of a deflectable catheter assembly having a catheter distal section that is deflectable by a tendon.

FIG. 1 illustrates one exemplary embodiment of a deflectable catheter assembly 100 that includes a compression compensation mechanism. The catheter assembly 100 comprises an elongated catheter shaft 101 having a catheter proximal section 104 and a catheter distal section 102. The catheter proximal section 104 may be further divided into two sections, a middle section 104' and a proximal section 104. Each section is constructed with different stiffness to optimize the performance of the catheter shaft 101. In one embodiment, the catheter distal section 102 is more flexible than the catheter proximal section 104. In the embodiment where the catheter proximal section 104 is divided into two sections, the middle section 104' is more flexible than the proximal section 104. Thus, the catheter distal section 102 is the most flexible section followed by the middle section 104'. The catheter proximal section 104 is the least flexible section of the catheter shaft 101. The middle section 104' and the proximal section 104 are used to transmit torque while the distal section 102 does the deflection for the catheter assembly 100. In one embodiment, the catheter assembly 100 is a deflectable catheter assembly.

In one embodiment, at least one tendon (see below) is disposed within the catheter shaft 101 to deflect the catheter distal section 102. Other techniques to deflect the catheter shaft 101 can also be incorporated and are known in the art. As shown in FIG. 1, when deflected, the catheter distal section 102 curls up to become a deflected section 102-D. A catheter handle 200 having a deflection control 202 is coupled to the catheter shaft 101 at the catheter proximal section 104. The catheter handle 200 includes a control mechanism to control the tendon that deflects the catheter distal section 102. The details of the control mechanism is described in the U.S. patent application Ser. No. 10/676,616 entitled “Deflectable catheter assembly and method of making same,” from which the present application is a continuation-in-part of as previously incorporated. At least one therapeutic tool such as a needle (see below) is disposed within the catheter shaft 101. One or more connection ports 204 may be provided at the catheter handle 200 to allow for necessary communication or connection to the therapeutic tool disposed within the catheter shaft 101. In some embodiments, only one therapeutic tool such as a needle is disposed within the catheter shaft 101. In those embodiments, only one connection port 204 is provided at the catheter handle 200. Other therapeutic tool such as an optical fiber bundle emitting light energy for therapies such as photodynamic therapy or a channeling tool to perform transmyocaridal revascularization can also be included in place of the needle or in addition to the needle.

Embodiments of the present invention pertains to a mechanism that deals with the problems of the movement of the therapeutic tool or the needle relative to the distal end of the catheter assembly 100 as a result of the catheter shaft 101 compression and relaxation. Compression and relaxation occurs for example, during insertion of the catheter shaft 101 into the body, needle retraction, deflection and/or deflection release of the catheter shaft 101, needle penetration into tissue, and the catheter shaft 101 extension and relaxation such as during the catheter shaft withdrawal and needle extension and during the needle advancement out of the catheter shaft 101. In addition, needle lumen path length may experience changes during the catheter shaft 101 rotation in a curved condition (if the needle is not on the central axis of the catheter).

In most therapeutic treatments, the therapeutic tool such as a needle is desired to remain retracted during the catheter shaft 101 insertion into (or removal from) the body. When inserting a long catheter shaft 101 into the body, the catheter shaft 101 is pushed through an introducer's seal and the inner diameter (ID) of the introducer and/or the ID of other devices such as a guiding catheter. The introducer, the seal, and other devices rub against the catheter shaft 101's outer diameter (OD). The catheter shaft 101 may also include a guidewire lumen, the ID of which will rub against the guidewire during insertion. Additionally, the catheter shaft 101 must be pushed around curves at the exit of the introducer and within the anatomy. These various factors create forces that cause the catheter shaft 101 to compress and thus shorten its length. In some cases, the catheter assembly 100 is a deflection catheter that deflects due the pulling on a tendon (or due to other types of deflection mechanisms); the force applied to the tendon for the pulling causes the shaft 101 to compress. As mentioned, the catheter assembly needs not be a deflection catheter to make use of the embodiments of the present invention. During these manipulations it is most desirable for the therapeutic tool or the needle to remain retracted (inside the catheter shaft 101). For example, if the therapeutic tool or the needle were allowed to extend outside the sheath, the therapeutic tool or the sharp point of the needle could engage the introducer and/or other devices and/or the tissue causing damage to the devices or the therapeutic tool/needle, injury to the patient and impeding or preventing the successful completion of the procedure (injection(s) in the desired tissue locations).

The compressive forces on the catheter shaft 101 cause the catheter shaft 101 to shorten. On the other hand, the compressive forces are not substantial compressive forces on the needle or the therapeutic tool; thus, the needle or the therapeutic tool remains at substantially the same length. Indeed, even if the compressive forces could be somehow be equalized, the catheter shaft 101 is generally made of a flexible plastic which has a much lower modulus than the generally metallic needle or therapeutic tool, thus the catheter shaft 101 will shorten much more than the needle or the therapeutic tool. Stiffening the catheter shaft 101's longitudinal modulus by incorporating a braid(s), spring(s) or other components can reduce (but not eliminate) the amount of catheter shaft 101 shortening, but at the cost of more construction complexity, larger OD's and/or increased catheter shaft 101's flexural stiffness.

Figure 2:
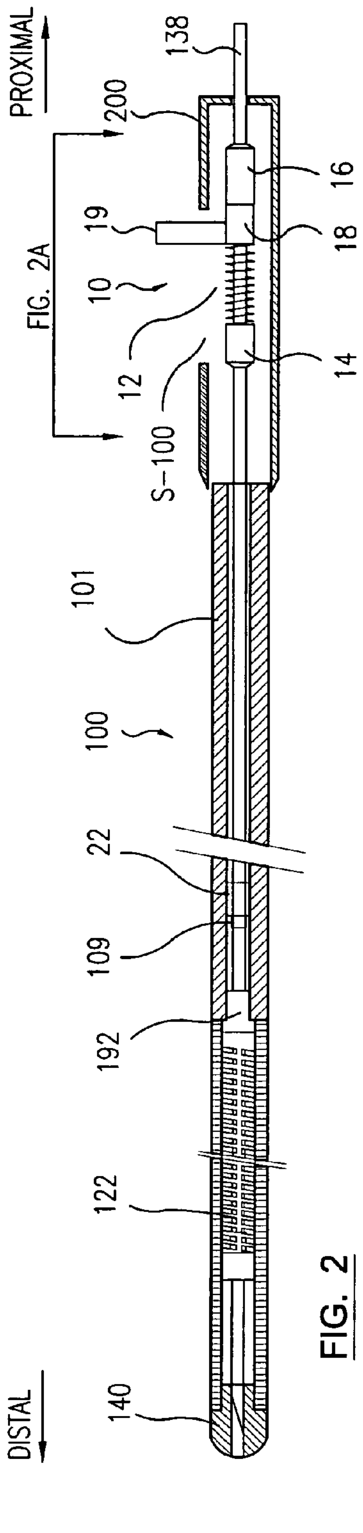
FIGS. 2-4, 2A, 2B, and 3A illustrate an exemplary embodiment of a catheter assembly having a compression compensation mechanism coupled to a needle.
Figure 3:
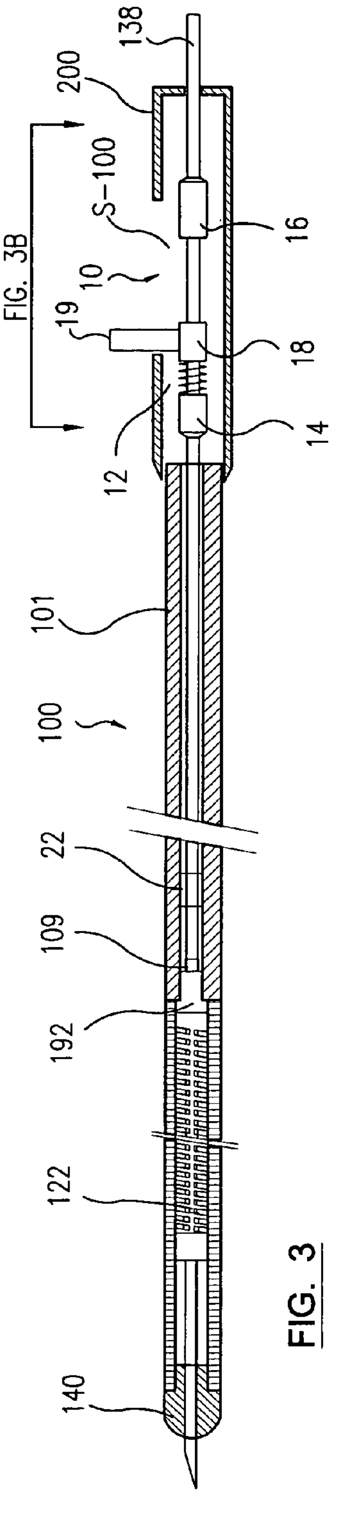
Figure 4:
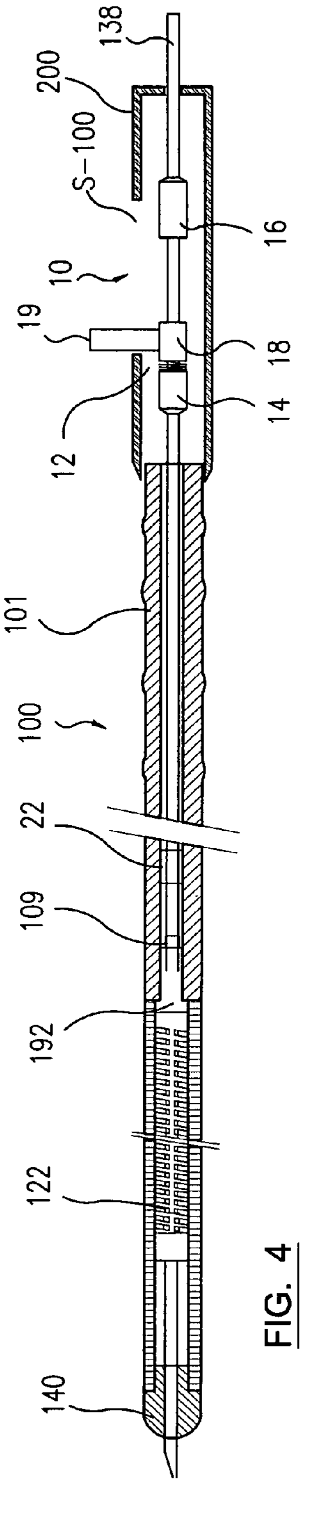

As shown in FIGS. 2-4, in one embodiment, a compression compensation mechanism 10 is coupled to the therapeutic tool to compensate for the compression caused to the catheter shaft 101 of the catheter assembly 100 (FIG. 1). In one embodiment, the therapeutic tool is a needle 138. The needle 138 can be disposed in the catheter shaft 101. The compression compensation mechanism 10 is included at the proximal end 138-P of the needle 138. In one embodiment, the compression compensation mechanism 10 is disposed within the handle 200. The compression mechanism 10 is configured to move the needle 138 in response to the compression of the catheter shaft 101 to compensate for the compression of the catheter shaft 101.

In FIGS. 2-4, the handle 200 is shown to be coupled to the proximal end 138-P of the catheter shaft 101. The ID of the catheter shaft 101 communicates with the ID of the handle 200, such that the needle 138 is slidably contained with the ID of the handle 200. A deployment slide 18 is constrained by the needle 138 such that the deployment slide 18 must remain engaged with the needle 138, but is free to slide proximally and distally over the outer diameter of the needle 138 and within the ID of the handle 200. The deployment slide 18 has a projection, lever, or a control 19, which is slidably constrained within a slot S-100 provided on the handle 200.

Figure 2B:
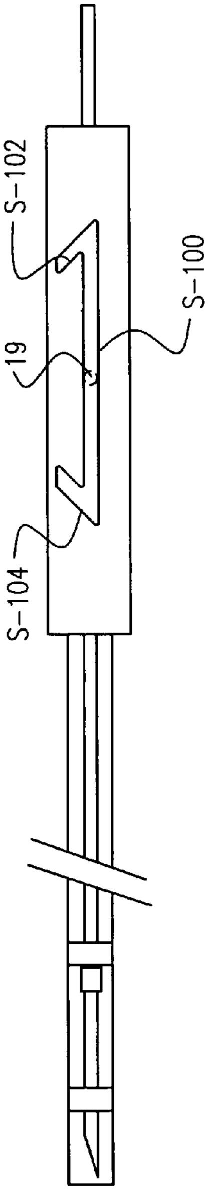
Figure 3A:
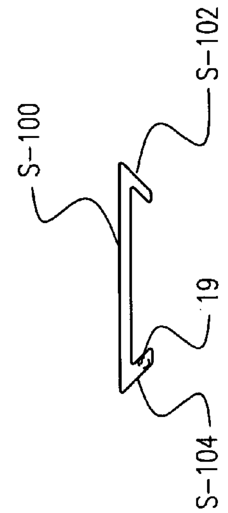
Figure 2A:
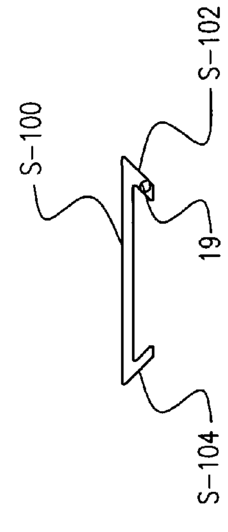

FIG. 2A illustrates a top view of the handle 200 that shows the slot S-100. In one embodiment, the slot S-100 includes a proximal recess slot portion S-102 and a distal recess slot portion S-104. The deployment slide 18 slides along the slot S-100 and can be locked into position either at the proximal recess slot portion S-102 and the distal recess slot portion S-104. The needle 138 is placed in the retracted position by moving the control 19 proximally in the slot S-100 and sliding/rotating the control 19 into the proximal recessed slot portion S-102 (as shown in FIG. 2A). The needle 138 is placed in the extended position by moving the control 19 distally in the slot S-100 and sliding/rotating the control 19 into the distal recessed slot portion S-104 (as shown in FIG. 3A). FIG. 2B illustrates top view of the slot S-100 in the handle 200 showing the control 19 of the deployment mechanism 18 that can be slide into the proximal recess slot portion S-102 or the distal recess slot portion S-104 to put the therapeutic tool into a recess position (proximal recess slot portion S-102) or an extended position (distal recess slot portion S-104).

The compression mechanism includes a distal stop 14, a proximal stop 16, and a spring 12. The distal stop 14 is a step on the OD of the needle 138 or a component attached to the OD of the needle 138. The proximal stop 16 is also a step on the OD of the needle 138 or a component attached to the OD of the needle 138. Both the distal stop 14 and the proximal stop 16 are slidably contained within the ID of the handle 200. In one embodiment, the spring 12 is constrained by the needle 138 such that the spring 12 remains engaged with the needle 138, but is free to extend and compress proximally and distally over the OD of the needle 138 and within the ID of the handle 200.

The deployment slide 18 can be a convenient mechanism that is used to move, extend or retract, the needle 138. The deployment slide 18 is coupled to the needle 138. In one embodiment, the control 19 on the deployment slide 18 is configured to protrude out of the handle 200 through the slot S-100 such that the physician or operator can access to extend or retract the needle 138. Alternatively, the deployment slide 18 can include a screw mechanism that is exposed through the handle 200 to allow the physician or operator to extend or retract the needle 138. Alternatively yet, the deployment slide 18 can be any conventional deployment slide that can be used to move the needle 138 within the catheter shaft 101.

Still with FIGS. 2-4, in one embodiment, the needle 138 further includes a needle stop mechanism 21 to control the travel distance of the needle 138. The needle stop mechanism 21 includes an interference 109 that cooperates with a distal needle hard stop 192 to control the extension distance of the needle 138. The interference 109 can be soldered or bonded to the needle 138 or otherwise attached to the outer surface of the needle 138. The interference 109 can be a step on the OD of the needle 138 and/or an attached component of suitable dimensions and properties. In one embodiment, the distal needle hard stop 192 is attached or mounted in the catheter shaft 101 inner surface. In an alternative embodiment, the distal needle hard stop 192 is attached or mounted in a needle lumen provided within the catheter shaft 101 for the needle 138 to be disposed therethrough. The distal needle hard stop 192 can be a step and/or an attached component of suitable dimensions and properties in the ID of the catheter shaft 101 or in the needle lumen provided within the catheter shaft 101.

As the interference 109 meets or engages the distal needle hard stop 192, the needle 138 is prevented from advancing (or moving distally) any further where the interference 109 meets the distal needle hard stop 192. The stop 192 and the interference 109 thus provide a control mechanism for the distal extension distance for the needle 138. FIG. 3 illustrates that the needle 138 extends a fixed distance 20. The stop 192 and the interference 109 cooperates to control the distal extension of the needle 138 and provides such fixed distance 20.

The interference mechanism 21 also includes a proximal needle hard stop 22 that cooperates with the interference 109 to control the retraction distance of the needle 138. In one embodiment, the proximal needle hard stop 22 is attached to or mounted in the catheter shaft 101 inner surface. In another embodiment, the proximal needle hard stop 22 is attached or mounted in the needle lumen's inner surface. The proximal needle hard stop 22 can be a step and/or an attached component of suitable dimensions and properties in the ID of the catheter shaft 101 or in the needle lumen provided within the catheter shaft 101.

As the interference 109 meets the proximal needle hard stop 22, the needle 138 is prevented from retracting (moving proximally) any further. The stop 22 and the interference 109 provide a control mechanism for the proximal retraction distance for the needle 138. The proximal needle hard stop 22 prevents the needle 138 from moving proximally undesirably or uncontrollably. For example, when the needle 138 is in its retracted position and when the catheter shaft 101 is being advanced, the catheter shaft 101 may experience compression during the advancement. Compression of the catheter shaft 101 causes the spring 12 to compress. This may cause the needle 138 to undesirably retract proximally. The proximal needle hard stop 22 would cooperate with the interference 109 to prevent the needle 138 from moving back (proximally) too far. It is often desirable to have the needle 138 be disposed within particular sections of the catheter shaft 101 for additional stiffness to aid in the delivery or maneuvering of the catheter assembly 100. Additionally, controlling the extension and retraction, or otherwise, movement of the needle 138 within the catheter shaft is desirable for precise and accurate deployment of the needle 138.

The interference mechanism 21 provides some compensation to the catheter shaft 101's compression. For example, as the catheter shaft 101 shortens due to the compression, the needle 138 can be pulled back (proximally) so that the interference 109 butts up against the proximal stop 22. The interference 109 and the proximal stop 22 follow the movement of the needle 138 as the catheter shaft 101 experiences compressions/shortening (and extensions/lengthening) that occur proximal to the proximal stop 22. The ID of the proximal stop 22 is configured to be smaller than the OD of the interference 109 to prevent the interference 109 from passing proximally through the proximal stop 22.

The compressions/shortening (and extensions/lengthening) that occurs in the catheter shaft 101 portions distal to the proximal stop 22 and proximal to the needles 138 distal exit point from catheter shaft 101 can affect the relative positions of the needle 138 tip and the shaft 101. Since the proximal stop 22 is mounted near the distal end of the catheter shaft 101, the affected length is very short and thus its compression/shortening length will be very short. The interference mechanism 21 thus effectively limits the relative motion between the needle 138 tip and its exit from the shaft 101. With the interference mechanism 21, the needle 138 tip may be safely positioned very near the needle's 138 exit from the shaft 101. It is to be understood that that the needle 138 may have the needle 138 exit at the distal tip of shaft 101, or at a port proximal to the distal end of the shaft 101.

In one embodiment, the spring 12 is mechanically constrained between the deployment slide 18 and the distal stop 14. In one embodiment, the spring 12 is fixedly attached at one end to the distal stop 14 and at the other end to the deployment slide 18. As the control 19 is moved proximally, it causes the deployment slide 18 to move proximally over the OD of the needle 138, decreasing the compression of the spring 12. The decreased compression of the spring 12 places a decreasing force in the distal direction on the spring stop 14. The force applied to the needle 138 is in the proximal direction. The decreased compression of the spring 12 allows the needle 138 to be moved in the proximal direction as shown in FIG. 2. The spring 12 is in the state of extension when the needle 138 is retracted in the proximal direction.

As the deployment slide 18 is moved in the proximal direction, the needle 138 moves in the proximal direction until the interference 109 engages the proximal stop 22. In one embodiment, after this engagement, the control 19 is moved further proximally and it is placed into the proximal recessed slot S-102 (FIG. 2A) in the handle 200. In this position, there is a controlled (by the component's designs) net force on the needle 138 biasing it in the proximal direction. The design of spring/spring mechanisms to provide desired forces over desired movement ranges is well known. This places the maximum compressive force that can be applied to the catheter shaft 101 by the operator (physician) during the needle 138 retraction under design control. The controlled compressive force on the catheter shaft 101 will improve the pushability of the catheter shaft 101 during insertion and positioning. The catheter shaft 101 will not compress further unless the external compressive forces on it exceed those applied to the needle138.

The control 19 is retained in the proximal recessed slot S-102 of the handle 200 until it is physically moved by the operator. The operator may release the control 19 into the proximal recessed slot portion S-102 and it will remain there (it would take an applied force to move it proximally enough to be rotated out of the proximal recess S-102). The operator thus has his hand free to perform other functions. As the length of catheter shaft 101 varies during the catheter shaft 101 manipulations, the positions of distal stop 14 and the proximal stop 16 will also vary in the same manner within the ID of handle 200. In a properly designed system, at the greatest compression of the catheter shaft 101, there will still be a net proximal force applied to the needle 138, such that the interference 109 and the stop 22 will be forced to remain engaged. Thus, the needle 138 will always remain fully retracted within the catheter body 101, when the control 19 is placed into the proximal recessed slot portion S-102.

Once the catheter shaft 101 is in the desired position, the needle 138 may be extended and penetrate body tissue to perform an injection or other therapeutic treatments (FIGS. 3 and 4). Since the distal end of the catheter shaft 101 cannot be seen, the needle 138 may be inadvertently extended too far into the tissue and the optimum injection point missed. Trying to view the needle 138 position using fluoroscopy in a properly designed catheter shaft 101 (e.g., as with radiopaque materials/markers incorporated) can be helpful to some degree, but the 2-D projection nature of fluoroscopy, lack of good soft tissue discrimination and its poor resolution of small objects make it very difficult to achieve good control. Exposure time to X-rays is also a limiting factor. Also, when attaching/detaching the syringe or other injection mechanism from the proximal end of the needle 138 and/or when actually making the injection, the needle's 138 extended length may be inadvertently and uncontrollably changed. In a catheter shaft, especially where the needle 138 extends out of the distal tip to the catheter shaft as the catheter shaft 101, the distal tip of the catheter shaft is often designed to contact, but not penetrate the tissue. Thus, to ensure that the needle 138 penetrated the tissue, it is often the practice to advance or otherwise manipulate catheter shaft to ensure that the distal tip of the catheter shaft has contacted the tissue. Often an Electrode Caridogram (ECG) electrode (insulated from an electrically conductive needle 138) is incorporated on the distal end of the catheter shaft 101 to determine tissue contact by ECG level in cardiac tissue. If the distal tip of the catheter shaft 101 were to be pushed against tissue, this would apply a compressive force on the catheter shaft 101 causing it to shorten. As described before, the needle 138 will not shorten as much and thus the effect will be to force the needle 138 deeper into the tissue in an uncontrolled manner. In the embodiments of the present invention, the interference mechanism 21 helps controlling the extension of the needle 138.

In addition, the compression compensation mechanism 10 moves the needle 138 as the catheter shaft 101 compresses or extends to compensate for the length change in the catheter shaft 101. As the control 19 is moved distally, it causes the deployment slide 18 to move distally over the OD of the needle 138, increasing the compression of the spring 12. The increased compression of the spring 12 places an increasing force in the distal direction on the spring stop 14. A force is applied to the needle 138 is in the distal direction. The needle 138 is forced to move in the distal direction until the interference 109 engages the distal stop 192. After this engagement, the control 19 is moved further distally and it is placed into a distal recess slot portion S-104 in the slot S-100 of the handle 200 (FIG. 3A). In this position, there is a controlled (by the component's designs) net force on the needle 138 biasing it in the distal direction. The design of spring/spring mechanisms to provide desired forces over desired movement ranges is well known. This places the maximum tensile force that can be applied to the catheter shaft 101 by the operator (physician) during needle extension under design control. In the extended position, the spring 12 places a proximal biasing force on the deployment slide 18 and thus on the control 19. The spring 12 is in the state of compression when the needle 138 is extended distally.

The biasing force retains the control 19 in the distal recessed slot S-104 until it is physically moved by the operator. The operator may release the control 19 into the distal recessed slot portion S-104 and it will remain there (it would take an applied force to move it distally enough to be rotated out of the recess). Thus the operator may remove his hand from the control 19 and the needle 138 will remain in the extended condition, so his hand is free to perform other functions. As the length of catheter shaft 101 proximal of the stop 192 varies during the catheter shaft 101 manipulations, the positions of the stops 14 and 16 will also vary in the same manner within the ID of the handle 200. In a properly designed system, at the greatest lengthening of the catheter shaft 101, there will still be a net distal force applied to the needle 138, such that the interference 109 and the stop 192 will be forced to remain engaged. Thus, the needle 138 remains fully extended out of the catheter shaft 101, when the control 19 is placed into the distal recessed slot portion S-104.

In one embodiment, as shown in FIG. 3, as the deployment slide18 is advanced distally, the spring 12 becomes more compressed against the proximal stop 14 to force the needle 138 to advance distally. The needle extension distance 20 is controlled by the distal stops 192 and 109 as previously mentioned. The spring 12 is not fully stacked or compressed thus giving the spring 12 more room to compress. When the catheter shaft 101 experiences compression that causes a length change, the spring 12 is compressed further as the needle 138 is pushed backward as shown in FIG. 4. Additionally, as the catheter shaft 101 compresses, the needle extension distance 20 remains constant while the remaining part of the needle 138 is pushed backward by the spring 12. The position of the deployment slide18 is relatively unchanged in that as the needle 138 is pushed back in the proximal direction, the deployment slide18 will not be pushed back into an undeployed position (proximal position) since the control 19 is locked in the distal recessed slot portion S-104 and since the spring 12 can be more compressed and stacked up to compensate for the movement in the needle 138 due to the shortening of the catheter shaft 138.

Without the spring 12 present, when the catheter shaft compresses, the needle 138 would not advance distally due to the stops 109 and 192 but in order to compensate for the compression, the deployment slide 18 would move proximally into an undeployed position. The deployment of the needle 138 will then be affected by the compression of the catheter shaft without the presence of the spring 12. In addition, the needle stop mechanism 21 may be affected as the interference 109 may press hard into the proximal needle hard stop 22 and damages the needle stop mechanism 21.

FIG. 4 illustrates also that as the catheter shaft 101 compresses, portions of the catheter shaft 101 may be slightly larger due to the shortening of the catheter shaft 101. With the presence of the spring 12, the position of the deployment slide18 having the control 19 is not affected by the catheter shaft compression.

Figures 5, 6, 7:
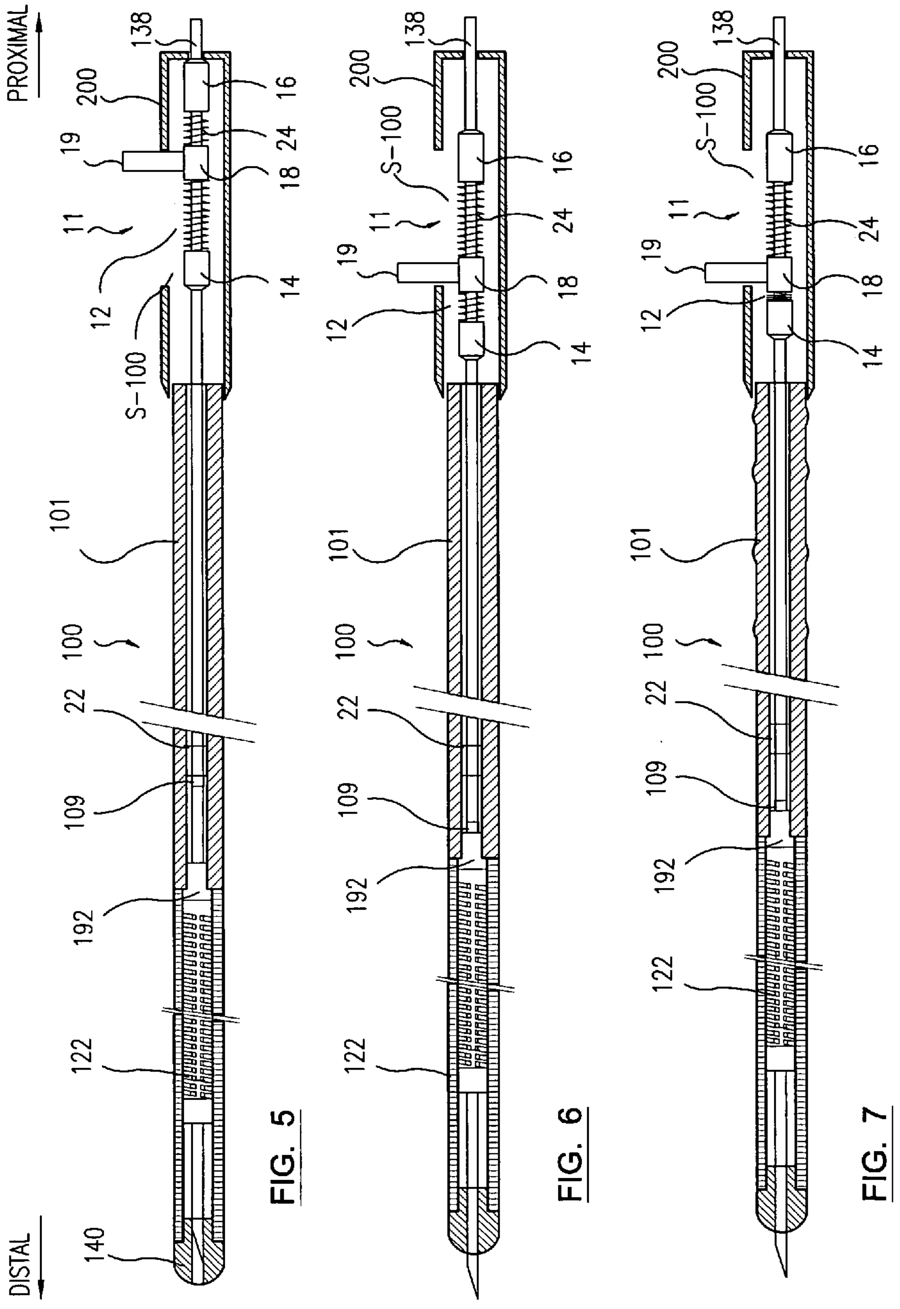
FIGS. 5-7 illustrate another exemplary embodiment of a catheter assembly having a compression compensation mechanism coupled to a needle.

FIGS. 5-7 illustrate an alternative embodiment of a compression compensation mechanism 11 that includes an additional spring 24. The compression compensation mechanism 11 is similar to the compression mechanism 10 previously described except for the addition of the additional spring 24. The embodiments shown in FIGS. 5-7 are similar to those shown in FIGS. 2-4 except for the compression compensation mechanism.

The compression mechanism includes a distal spring stop 14, a proximal spring stop 16, a distal spring 12, and a proximal spring 24. The distal spring stop 14 is a step on the OD of the needle 138 or a component attached to the OD of the needle 138. The proximal spring stop 16 is also a step on the OD of the needle 138 or a component attached to the OD of the needle 138. Both the spring stops 14 and 16 are slidably contained within the ID of the handle 200. In one embodiment, the distal spring 12 and the proximal spring 24 are constrained by the needle 138 such that they remain engaged with the needle 138, but are free to slide proximally and distally over the OD of the needle 138 within the ID of the handle 200. The needle 138 is placed in the retracted position by moving the control 19 proximally in the slot S-100 of handle 200 and sliding/rotating control 19 into a proximal recessed slot portion S-102 (as shown in FIG. 2A).

In one embodiment, the springs 12 and 24 are compression springs and are mechanically constrained between the slide 18 and one of the spring stops 14 and 16, respectively. As the control 19 is moved proximally, it causes the deployment slide 18 to move proximally over the OD of the needle 138, increasing the compression of the spring 24 and decreasing the compression of the spring 12. The increased compression of the spring 24 places an increasing force in the proximal direction on the spring stop 16 and a decreasing force in the distal direction on the spring stop 14. A net force is applied to the needle 138 is in the proximal direction. The needle 138 is forced to move in the proximal direction until the interference 109 engages the stop 22. After this engagement, the control 19 is moved further proximally and it is placed into the proximal recessed slot portion S-102 as shown in FIG. 5A. In this position, there is a controlled (by the component's designs) net force on the needle 138 biasing it in the proximal direction. The design of spring/spring mechanisms to provide desired forces over desired movement ranges is well known.

This places the maximum compressive force that can be applied to the shaft 101 by the operator (physician) during needle retraction under design control.

The controlled compressive force on the shaft 101 will improve the pushability of the catheter shaft 101 during insertion and positioning. The catheter shaft 101 will not compress further unless the external compressive forces on it exceed those applied to the needle138. In the retracted position, the proximal spring 24 places a distal biasing force on the deployment slide 18 and thus on the control 19. This biasing force retains the control 19 in the proximal recessed slot portion S-102 until it is physically moved by the operator.

As the length of the catheter shaft 101 proximal of the stop 22 varies during the catheter shaft 101 manipulations, the positions of the spring stops 14 and 16 will also vary in the same manner within the ID of the handle 200. At the greatest compression of catheter shaft 101, there will still be a net proximal force applied to the needle 138, such that the interference 109 and the stop 22 will be forced to remain engaged. Thus, the needle 138 will remain fully retracted within the catheter shaft 101 when the control 19 is placed into the proximal recessed slot portion S-102.

As the control 19 is moved distally, the slide 18 is moved distally over the OD of the needle 138, increasing the compression of the spring 12 and decreasing the compression of the spring 24. The increased compression of the spring 12 places an increasing force in the distal direction on spring stop 14 and a decreasing force in the proximal direction on the spring stop 16. A net force is applied to the needle 138 in the distal direction. The needle 138 is forced to move in the distal direction until the interference 109 engages the stop 192. After this engagement, the control 19 is moved further distally and it is placed into the distal recessed slot portion S-104. In this position, there is a controlled (by the component's designs) net force on the needle 138 biasing it in the distal direction. This places the maximum tensile force that can be applied to the shaft 101 by the operator (physician) during needle extension under design control. In the extended position, the spring 12 places a proximal biasing force on the slide 18 and thus on the control 19. This biasing force, retains the control 19 in the distal recessed slot portion S-104 until it is physically moved by the operator.

As the length of the catheter shaft 101 proximal of the stop 192 varies during the catheter shaft 101 manipulations, the positions of the spring stops 14 and 16 will also vary in the same manner within the ID of the handle 200. At the greatest lengthening of the catheter shaft 101, there will still be a net distal force applied to the needle 138, such that the interference 109 and the stop 192 will be forced to remain engaged. Thus, the needle 138 will remain fully extended out of the catheter shaft 101, when the control 19 is placed into the distal recessed slot portion S-104.

In an alternative embodiment, the springs 12 and 24 are extension springs that are mechanically attached between the deployment slide 18 and one of the spring stops 14 and 16, respectively. In yet another embodiment, the stops 14 and 16 are omitted and the ends of the springs 12 and 24 are directly attached to the needle 138. As the control 19 is moved proximally, the slide 18 moves proximally over the OD of the needle 138, increasing the extension of the spring 12 and decreasing the extension of the spring 24. The increased extension of the spring 12 places an increasing force in the proximal direction on the spring stop 14 and a decreasing force in the distal direction on the spring stop 16. A net force is applied to the needle 138 in the proximal direction. The needle is forced to move in the proximal direction until interference 109 engages stop 22. After this engagement, the control 19 is moved further proximally and it is placed into the proximal recessed slot portion S-102. In the retracted position, the spring 12 places a distal biasing force on slide 18 and thus on the control 19. This biasing force retains the control 19 in the proximal recessed slot portion S-102 until it is physically moved by the operator.

As the length of catheter shaft 101 proximal of the stop 22 varies during the catheter shaft 101 manipulations, the positions of the spring stops 14 and 16 will also vary in the same manner within the ID of the handle 200. In a properly designed system, at the greatest compression of shaft 101, there will still be a net proximal force applied to the needle 138, such that the interference 109 and the stop 22 will be forced to remain engaged. Thus, the needle 138 remains fully retracted within the catheter shaft 101 when the control 19 is placed into the proximal recessed slot portion S-102.

In the alternative embodiment, as the control 19 is moved distally, the deployment slide 18 moves distally over the OD of the needle 138, increasing the extension of the spring 24 and decreasing the extension of the spring 12. The increased extension of the spring 24 places an increasing force in the distal direction on the spring stop 16 and a decreasing force in the proximal direction on the spring stop 14, such that the net force applied to the needle 138 is in the distal direction. The needle is forced to move in the distal direction until the interference 109 engages the stop 192. After this engagement, the control 19 is moved further distally and it is placed into the distal recessed slot portion S-104. In the extended position, the spring 24 places a proximal biasing force on the deployment slide 18 and thus on the control 19. This biasing force, retains the control 19 in the distal recessed slot portion S-104 until it is physically moved by the operator.

As the length of catheter shaft 101 proximal of the stop 192 varies during catheter shaft 101 manipulations, the positions of the spring stops 14 and 16 will also vary in the same manner within the ID of the handle 200. A net proximal force is applied to the needle 138, such that the interference 109 and stop 22 will be forced to remain engaged. Thus, the needle 138 remains fully extended out of the catheter shaft 101, when the control 19 is placed into the distal recessed slot portion S-104.

FIG. 7 illustrates also that as the catheter shaft 101 compresses, portions of the catheter shaft 101 may be slightly larger due to the shortening of the catheter shaft 101. With the presence of the spring 12, the position of the deployment slide18 having the control 19 is not affected by the catheter shaft compression.

One advantage of including a compression compensation mechanism such as the compression compensation mechanism 10 or 11 is that relying on the needle stop mechanism alone to address the shaft length change may be insufficient. For instance, when the catheter shaft 101 compresses, having the operator pulls back on the needle 138 requires the operator to be careful not to pull the interference 109 against the stop 22 too hard and cause the relative motion of the needle stop mechanism 21 to fail (the inference 109 may be forced through the ID of the stop 22) or the mechanism 21 to lock up (the interference 109 may be jammed in the ID of the stop 22). In addition, the operator may cause the compression force to be applied to the portion of the catheter shaft 101 proximal to the stop 22 causing the catheter shaft 101 to fail or be shortened to such a high degree that, when the catheter shaft 101 is released, the distal portions of catheter shaft 101 jumps forward and cause injury and/or, in a deflection catheter, significantly changes the tendon path length and thus the curvature of the deflected portion. The catheter shaft 101, the stop 22 and the interference 109 may be made bigger to withstand the greatest force expected, but only at the cost of larger/more expensive/potentially stiffer components and even then the potential for a failure under extraordinary conditions still exists. In addition, it is clumsy to require the operator to continuously pull back on the needle138 during all of the catheter shaft 101 manipulations. He needs his hands free to perform functions like guiding the catheter shaft 101 into the introducer while holding the introducer or guiding catheter in position or rotating and deflecting the catheter shaft 101 while holding the introducer or guiding catheter in position. Having another operator assist will work, but this is an expensive and clumsy solution.

It is to be appreciated that while the following discussed the incorporation of the compression compensation mechanism 10 or 11 into a deflectable catheter assembly that is deflected by a tendon, the compression compensation mechanism 10 or 11 can be incorporated into other catheter assembly where the catheter shaft may be compressed (even though not necessarily deflected) during deployment such that controlling the extension distance of the needle or tool included within the catheter shaft is necessary. As discussed, the needle or the tool can be configured to include the compression compensation mechanism 10 or 11 at the proximal end. A handle that is used to control the needle can house the compression compensation mechanism 10 or 11. In addition, although the discussion focuses on the compression compensation mechanism 10 or 11 being attached to the needle 138, it is to be understood that the compression compensation mechanism 10 or 11 can be similarly used on other internal devices of the catheter assembly 100.

Figure 8:
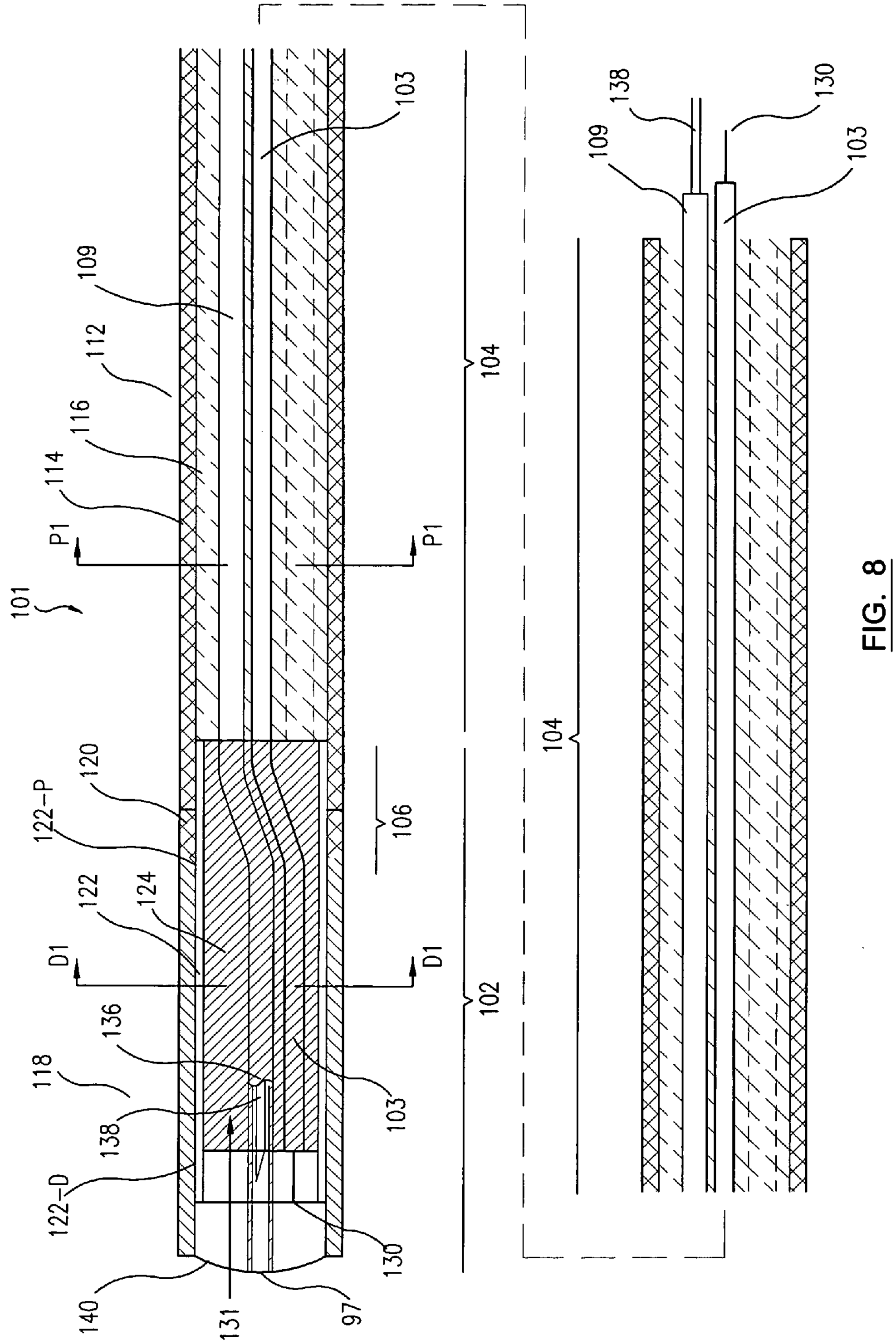
FIG. 8 illustrates a deflectable catheter assembly with the tendon being placed in the center along the catheter proximal section and brought to the side at the catheter distal section.

FIG. 8 illustrates a side view of the catheter shaft 101 of the catheter assembly 100. The description below is only an example of a catheter assembly that will benefit from the compression compensation mechanism 10 or 11. Other catheter assemblies such as those known in the art can very well include therapeutic tools or needles that are configured to include the compression compensation mechanism 10 or 11. The catheter shaft 101 includes a tendon 130 and a needle assembly 109, which includes a needle 138 and a compression compensation mechanism 10 or 11. The compression compensation mechanism 10 or compression compensation mechanism 11 can be coupled to the proximal end of the needle 138 as previously described. The tendon 130 and the needle assembly 109 are disposed within a central lumen 131 and extend continuously from the catheter distal section 102 to the catheter proximal section 104. At the catheter proximal section 104, the tendon 130 is located in the center (or approximately in the center) and the needle assembly 109 is located off-center of the catheter shaft 101. It is to be appreciated that the catheter assembly 100 may include more than one needle assembly each having a compression compensation mechanism previously described. Alternatively, other therapeutic or diagnostic tools may replace the needle assembly 109 or may be included in addition to the needle assembly 109. Other therapeutic tool such as an optical fiber bundle emitting light energy for therapies such as photodynamic therapy or a channeling tool to perform transmyocaridal revascularization can also be included in place of the needle or in addition to the needle assembly 109. In one embodiment, the therapeutic tool is configured to include the compression compensation mechanism as previously described for the needle 138.

Figure 9:
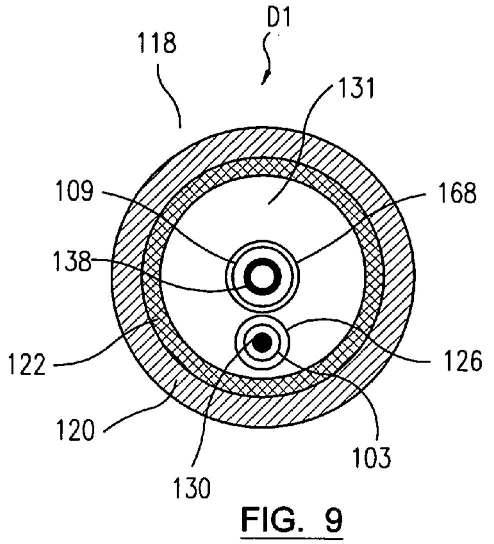
FIG. 9 illustrates a cross-sectional view of the catheter distal section of the catheter assembly illustrated in FIG. 8.
Figure 10:
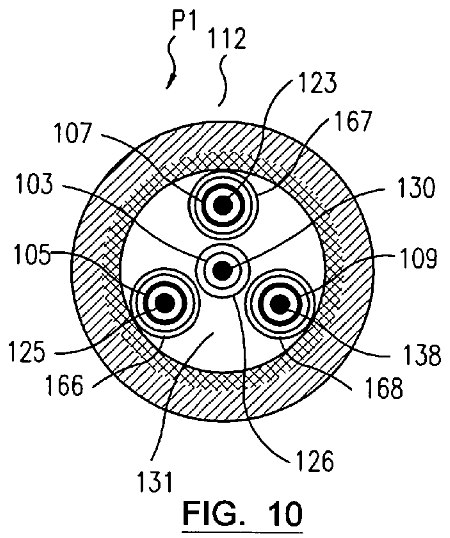
FIG. 10 illustrates a cross-sectional view of the catheter assembly illustrated in FIG. 8 along the catheter proximal section.

In one embodiment, each of the tendon 130 and the needle assembly 109 is disposed within a lumen provided within the central lumen 131 of the catheter shaft 101 (FIGS. 9-10). The tendon 130 is disposed within a tendon lumen 126 and the needle assembly 109 is disposed within a needle lumen 168.

FIG. 9 shows a cross-section D1 of the distal catheter shaft 118. As shown in FIG. 9, the tendon 130 is located off-center of the distal catheter shaft 118; and, the needle assembly 109 is located approximately in the center of the distal catheter shaft 118. The tendon 130 needs to be off-center to be able to deflect the distal section 102 of the catheter assembly 100. The tendon 130 is disposed within the tendon lumen 126, which is positioned off-centered in the distal catheter shaft 118. The needle assembly 109 is disposed within the needle lumen 168, which is a positioned approximately in the center of the distal catheter shaft in one embodiment. The central lumen 131 may be filled with polymer to secure the tendon 130 and the needle assembly 109. Surrounding the central lumen 131 is a compression cage 122 (details below) and surrounding the compression cage 122 is a distal jacket 120 that defines the outer diameter for the distal catheter shaft 118. The distal catheter shaft 118 may have more lumens disposed therein to house additional tools, components, or needle assemblies if necessary.

FIG. 10 shows a cross-section P1 of the proximal catheter shaft 112. As shown in FIG. 10, the tendon 130 is located approximately in the center of the proximal catheter shaft 112. In some embodiments, the proximal catheter shaft 112 have several off-center lumens, lumens 166, 167, and 168, formed therein. The needle lumen 168 is occupied by the needle assembly 109 as previously mentioned. Both or none of the lumens 166 and 167 may be occupied by additional needle assembly (e.g., a needle assembly 105 having a needle 125 and a needle assembly 107 having a needle 123), or alternatively by a lumen filler. Having the additional off-center lumens provides a balance to the proximal catheter shaft 112. When the lumens 166 and 167 are included for balancing purpose, they need not be extended into the distal catheter shaft 118 as the tendon lumen 126.

Returning to FIG. 8, the details the configuration of components of the deflectable catheter assembly 100 are shown. In FIG. 8, the catheter shaft 101 is divided into two sections referred to as a proximal catheter shaft 112 and a distal catheter shaft 118.

The distal catheter shaft 118 includes a distal core shaft 124 and the proximal catheter shaft 112 includes a proximal core shaft 116. Each of the distal core shaft 124 and the proximal core shaft 116 is made of a polymer such as polyether block amides (Pebax®; Pebax is a registered trademarks of Ato Fina Chemicals), Nylon, or Polyurethane. The material used for the distal core shaft 124 is more flexible (e.g., lower in hardness durometer) than the material used for the proximal core shaft 116.

In some embodiments, the proximal catheter shaft 112 is further divided into a middle catheter shaft (not labeled) and the proximal catheter shaft 112. The middle catheter shaft and the proximal catheter shaft 112 are constructed similarly but may have different flexibilities. When being used, the proximal catheter shaft 112 lays in relatively straight sections of the vascular anatomy such as the femoral arteries and the aorta. The proximal catheter shaft 112 functions mainly to transmit torque. Therefore, the proximal catheter shaft 112 is the stiffest section of the catheter assembly 100. The middle catheter shaft may lie around an arch section such as the aortic arch. The middle catheter shaft thus has to transmit torque over a curve. Therefore, the middle catheter shaft has to be relatively flexible compared to the proximal catheter shaft 112. To create the proximal catheter shaft 112 with different stiffness sections, different durometer materials are used for the proximal catheter shaft 112. For example, the proximal catheter shaft 112 can be constructed with high durometer materials such as Nylon12 and Pebax72D while the middle catheter shaft can be constructed with slightly lower durometer materials such as Pebax63D, a blend of Pebax63D, or even lower durometer Pebax materials.

As illustrated in FIG. 8, at the catheter proximal section 104, the outer most layer of the catheter shaft 101 is the proximal catheter shaft 112 which functions as a torque shaft that can deliver torque from a proximal handle manipulation to the catheter distal section 102. In one embodiment, the proximal catheter shaft 112 is made of a polymer tube reinforced with a support braided layer 114 made of braided wires embedded within a support polymer layer. The support braided layer 114 can have forms of wires and ribbon, round or flat and can be made of metals such as stainless steel, NiTi, or strong polymer such as Nylon, and Peek. The wire cross-section of the wires in the layer 114 can be round, rectangular, or any other suitable shape. The support polymer layer can be made of polymers commonly used in catheter construction such as Nylon, Pebax, Polyurethane, Polyolefin, etc.

The distal catheter shaft 118 is a flexible section that allows the catheter distal section 102 to deflect when the tendon 130 is pulled. The distal catheter shaft 118 includes a layer of a low durometer material such as a low durometer Pebax. The low durometer material used for the distal catheter shaft 118 has a lower hardness scale compared to the proximal catheter shaft 112 for example, the material used for the distal catheter shaft 118 may have a hardness scale of about 35D.

The distal catheter shaft 118 has at least two functions: to house the distal portions of the internal components of the catheter assembly 100 and to facilitate the deflection of the catheter distal section. As illustrated in FIGS. 8-9, the distal section 102 is comprised of two components: a distal jacket 120, a compression cage 122 and a distal core shaft 124. The distal jacket 120 acts as an outer packaging layer for the internal components of the catheter assembly 100 that are housed in the catheter distal section 102. It is made of polymeric materials such as Nylon, Pebax, Pebax blend and low durometer material. In order to facilitate a bias to deflect the catheter distal section 102, the distal catheter shaft 118 needs to be made of lower durometer and more flexible materials than those used for the catheter proximal section 112 to allow the tendon 130 to deflect the distal catheter shaft 118 when being pulled.

The following sections describe in details the construction of the catheter assembly 100. The catheter assembly 100 is constructed in the order of constructing the inside components to the outside components. In addition, the catheter proximal section 104 and the catheter distal section 102 are constructed separately and joined together to form the catheter assembly 100.

Figure 11:
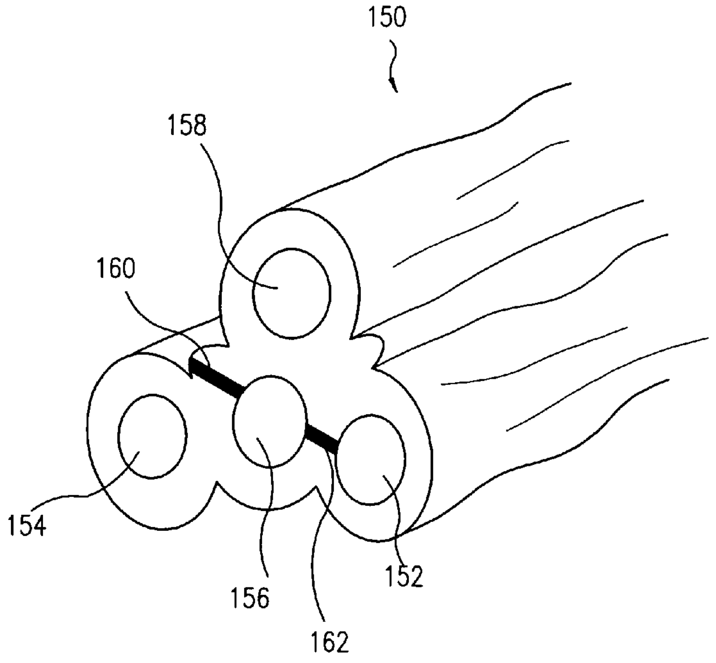
FIGS. 11-14 illustrate simplified three-dimensional views of exemplary methods of making the catheter assembly illustrated in FIG. 2.

In FIG. 11, a multi-lumen extruded tube 150 is provided for the preparation of the distal catheter shaft 118. The multi-lumen extruded tube 150 will later form a distal core shaft 124 for the catheter distal shaft 118. In one embodiment, the multi-lumen tube 150 includes lumens 152, 154, 156, and 158 with the lumen 156 being in the central lumen while the lumens 152, 154, and 158 are located radially around the lumen 156. It is to be appreciated that more or less lumens than shown in FIG. 11 may be used depending on how many lumens are needed for the catheter shaft 101. A slit is cut into the lumen 156 and into one of the side lumens (e.g., the lumen 152). This is done so that the tendon assembly 103 can be transitioned from the center of the catheter shaft 101 to the side of the catheter shaft 101 in order to deflect the catheter distal section 102 when the tendon 130 is being pulled. In addition, the needle assembly 109 can also be transitioned from the side of the catheter shaft 101 into the center of the catheter shaft 101. In one embodiment, a first slit 160 is cut into the central lumen 156. The first slit 160 has a length that covers most of the length of the multi-lumen extruded tube 150 except for a short distance (e.g., 0.5-1.5 cm) from the proximal end of the tube 150. A second slit 162 is cut through the wall between the side lumen 152 and the central lumen 156. The second slit 162 is located on the oppose side of the first slit 160. The second slit 162 has a length that covers most of the length of the multi-lumen extruded tube 150 except for a short distance (e.g., 0.5-1.5 cm) from the proximal end of the tube 150. The first slit 160 is formed to allow the tendon assembly 103 to move from being in (or approximately in) the center of the catheter shaft 101 to the side of the catheter shaft 101 at the distal catheter shaft 118. The second slit is formed to allow the needle assembly 109 to move from an off-center location to an approximately center location.

Figure 12:
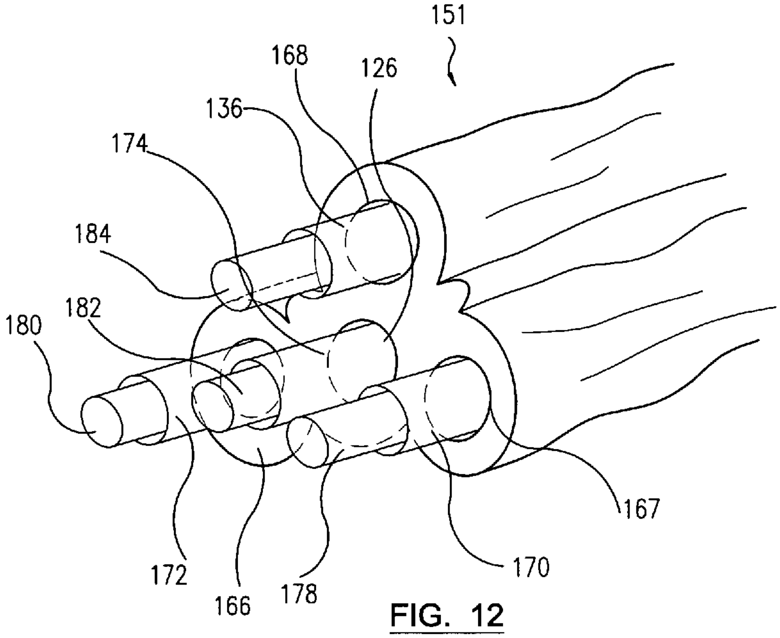

In FIG. 12, a multi-lumen extruded tube 151 is provided for the preparation of the proximal catheter shaft 112. The multi-lumen extruded tube 151 will later form the proximal core shaft 116 for the catheter proximal shaft 112. In one embodiment, the multi-lumen extruded tube 151 includes a tendon lumen 126, needle lumens 166, 167, and 168, with the tendon lumen 126 being in the central lumen while the needle lumens 166, 167, and 168 are located radially around the lumen 126. It is to be appreciated that more or less lumens may be used depending on how many lumen are needed for the catheter assembly 100. Low-friction liners are inserted into the lumens: a liner 174 is inserted into the tendon lumen 126; a liner 136 is inserted into the needle lumen 168; a liner 170 is inserted into the needle lumen 167; and, a liner 172 is inserted into the needle lumen 166. In one embodiment, the liners are made of polytetrafluoroethylene (PTEF) or TEFLON® (TEFLON is a registered trademark of Dupont), high-density polyethylene (HDPE), polyetheretherketone (PEEK), or polyimide with a somewhat lubricious lumenal wall. The liners allow the tendon 130, the needle assemblies, and/or other therapeutic tools to move easily within the lumens. A mandrel is inserted into each of the liners to define the inner diameter of each lumen: a mandrel 182 is inserted into the liner 174; a mandrel 180 is inserted into the liner 172; a mandrel 178 is inserted into the liner 170; and, a mandrel 184 is inserted into the liner 136. Each of the liners 136, 170, 172, and 174 may be chemically treated (e.g., etched) to increase adhesion of the liners to the polymer of the tubes 151 and 150.

In embodiments where some of the lumens are included only for balancing purposes, the liners and mandrels will not be extended into the lumens in the distal catheter shaft 118. After the final heat fusion, the extra lumens in the distal catheter shaft 118 are closed since there is no liner and mandrel to keep the lumen open. Balancing of the catheter shaft 101 is only needed in the proximal catheter shaft 112.

Figure 13:
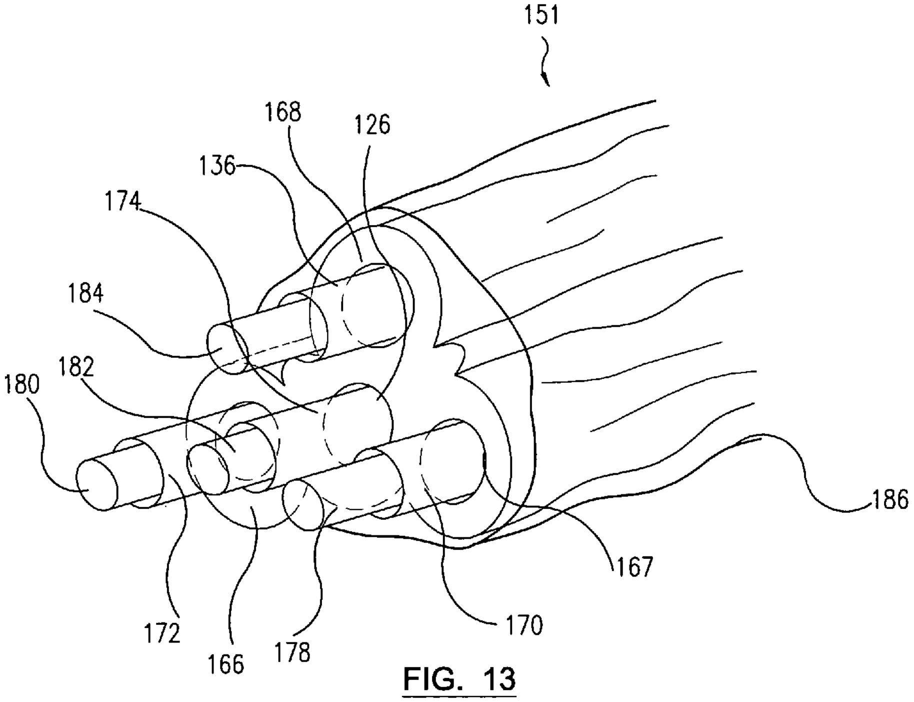

In FIG. 13, a shrink tube 186 is placed over the tube 151 that now has the liners and mandrels and the whole assembly is reformed under a heat source. The heated polymer melts and collapses onto the liners under the compression of the shrink tube 186 forming a multi-lumen proximal core shaft 116. The shrink tube helps define the outer diameter of the proximal core shaft 116 while the mandrels define the inner diameter of the lumens.

Figure 14:
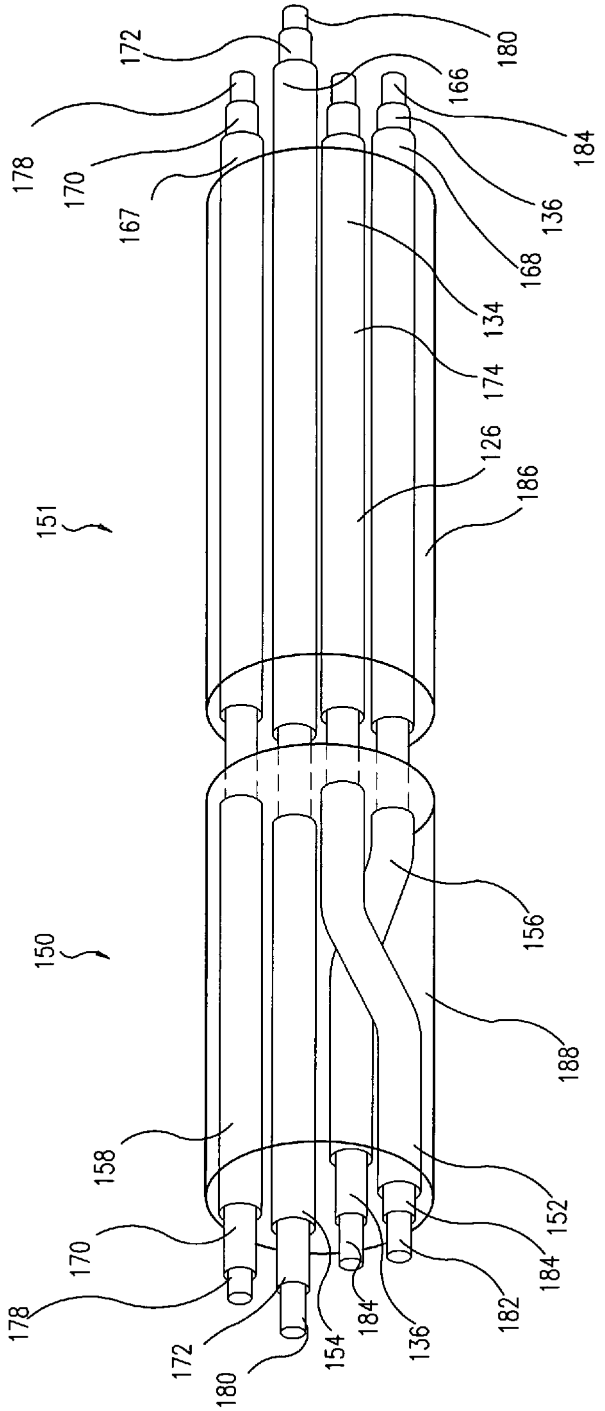

Next, as shown in FIG. 14, the distal core shaft (the multi-lumen extruded tube 150) is coupled to the proximal core shaft (the multi-lumen extruded tube 151). The mandrels and the respective extra length of the liners 136, 170, 172, and 174 originally over hanging from the multi-lumen extruded tube 151 are inserted into the lumens of the multi-lumen extruded tube 150. At the proximal end of the first slit 160, the line 174 and the mandrel 182 are brought out of the central lumen 156 and placed along the wall space made by the first slit 160. This will form the off-center tendon lumen 126 (shown in FIGS. 8-9) in the catheter distal section 102 after a heat fusion process. The tendon 130 is later disposed within the tendon lumen 126 as will be described below.

Also in FIG. 14, each of the liners 136, 170, and 172 (along with their respective mandrels) is inserted into one of the side lumens. In one embodiment, at the proximal end of the second slit 162, the liner 136 and the mandrel 184 are brought into the center of the tube 150 to prepare for the forming of a central lumen 164. This will form the center needle lumen 164 for the catheter distal section 102.

Next, the distal core shaft 124 and the proximal core shaft 116 are formed. In FIG. 14, a shrink tube 188 is placed over the multi-lumen 150 of the multi-lumen tube 151. The shrink tube 188 defines the outer diameter of the distal core shaft 124. The shrink tube 186 that defines the outer diameter of the proximal core shaft 116 is also placed over the multi-lumen 150 as illustrated in FIG. 14. The structure is placed under a heat source. The polymer melts and collapses into the support mandrels under the compression from the shrink tubes 188 and 186, allowing for the formation of the distal core shaft 124 and the proximal core shaft 116. After the heat fusion process, the shrink tubes 188 and 186 are removed from the formed distal core shaft 124 and the proximal core shaft 116.

Next, the distal catheter shaft 118 and the proximal catheter shaft 112 are formed. In one embodiment, a compression cage 122 (details below) is placed over the distal core shaft 124 (FIGS. 8-9). A support braided layer 114 is placed over the proximal core shaft 116 (FIG. 8). The support braided layer 114 can be made of materials such as stainless steel, Nylon, PEEK, or cold worked Nitinol. A layer of support polymer that will form the distal jacket 120 is placed over the compression cage 122. An outer shrink tube (not shown) is then placed over the support polymer. In addition, a layer of support polymer is placed over the support braided layer 114 and an outer shrink tube is placed over the polymer layer. After heat fusion, the polymer will embed the braided layer 114 there within. These outer shrink tubes define the outer diameter of the catheter shaft 101. The outer shrink tubes are removed after the heat fusion that completes the distal catheter shaft 118 and the proximal catheter shaft 112.

In one embodiment, for the distal catheter shaft 118, heat is applied only to the two ends of the outer shrink tube that covers the distal jacket 120. After the heat fusion process, only the two ends of the compression cage 122 is attached to the distal jacket 120. The compression cage 122 is thus allowed to move more freely within the distal jacket 120. The compression cage 122 thus allows the internal components within catheter distal section 102 to move during deflection thus lowering the deflection stiffness.

For the proximal catheter shaft 112, heat is applied across the entire length of the outer shrink tube. The polymer fuses into the support braided layer 114 forming the proximal catheter shaft 112.

The mandrels can be removed after the catheter shaft 101 is formed. After the mandrels are removed, the lumens are vacant. The internal components of the catheter assembly 100 can then be'disposed within the catheter shaft 101 as necessary. Unoccupied lumens can be filled with lumen fillers to maintain balance for the catheter shaft 101 if necessary.

The compression cage 122 and method of making the same is described in details in U.S. 20020165461 now U.S. Pat. No. 6,585,718, which is hereby incorporated by reference in its entirety. The compression cage 122 functions to maintain the axial length of the catheter distal section 102, prevents stretching of the catheter distal section 102, resists prolapse or kinking of the catheter distal section 102, maintains inner lumen integrity for the catheter distal section 102, and provides support for therapeutic tool engagement with the anatomy. The compression cage 122 is configured to resist axial and radial compression loads while maintaining flexibility.

Figure 15:
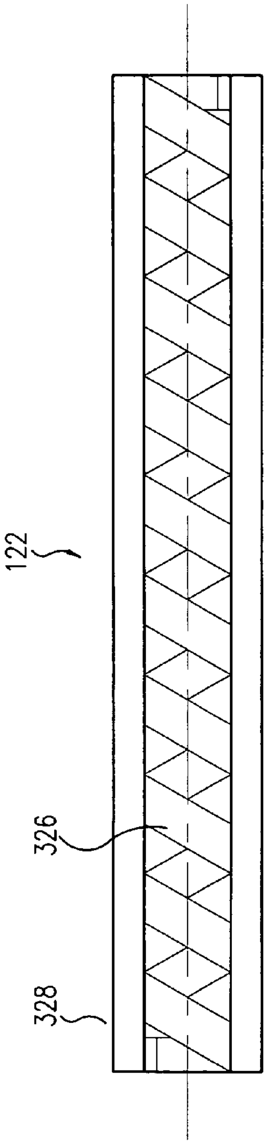
FIGS. 15-19 illustrate various configurations of a compression cage that can be used to resist compression of the catheter distal section of a deflectable catheter assembly.
Figure 16:
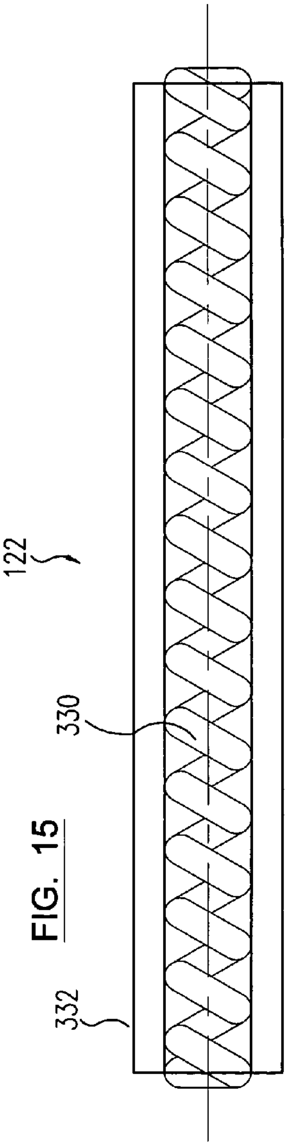
Figure 17:
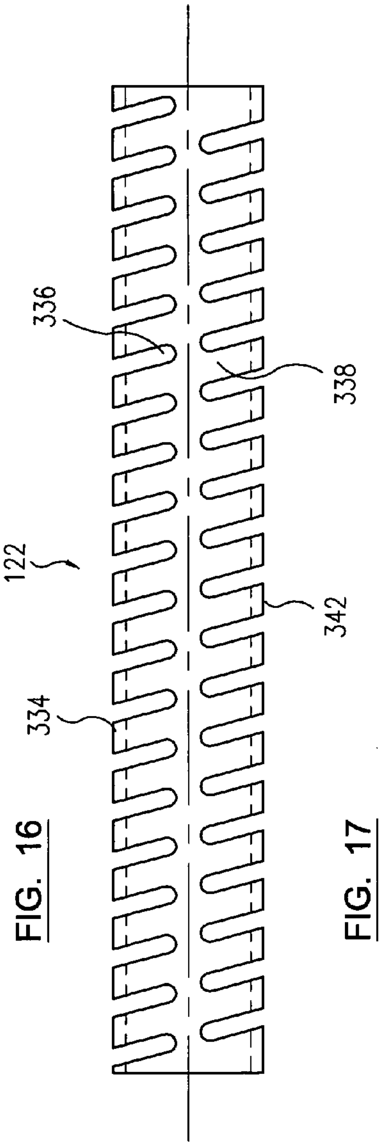

Various configurations of the compression cage 122 can be seen in FIGS. 15-17. The compression cage 122 includes a proximal end 122-P, a distal end 122-D, and a central lumen 122-L there between. The compression cage 122 is ideally made from a resilient material, such as Nitinol, spring-temper austenitic stainless steel, or heat-treatable stainless steel so that upon unloading it tends to return to a pre-established shape, such as straight. In some embodiments, the compression cage 122 is configured to be a stent-like structure using the material mentioned above such as NiTi, stainless steel, or other metallic alloy.

In one embodiment, as illustrated in FIG. 15, the compression cage 122 includes a flat-wire coil 326 and two substantially longitudinal struts 328. The struts 328 are diametrically opposed to each other and are welded, soldered, brazed, adhered, or otherwise attached to some or all loops of the coil 326.

In another embodiment, as illustrated in FIG. 16, the compression cage 122 includes a round-wire coil 330 and two substantially longitudinally struts 332. The struts 332 are diametrically opposed to each other and are welded, soldered, brazed, adhered, or otherwise attached to some or all loops of the coil 330.

Figure 18:
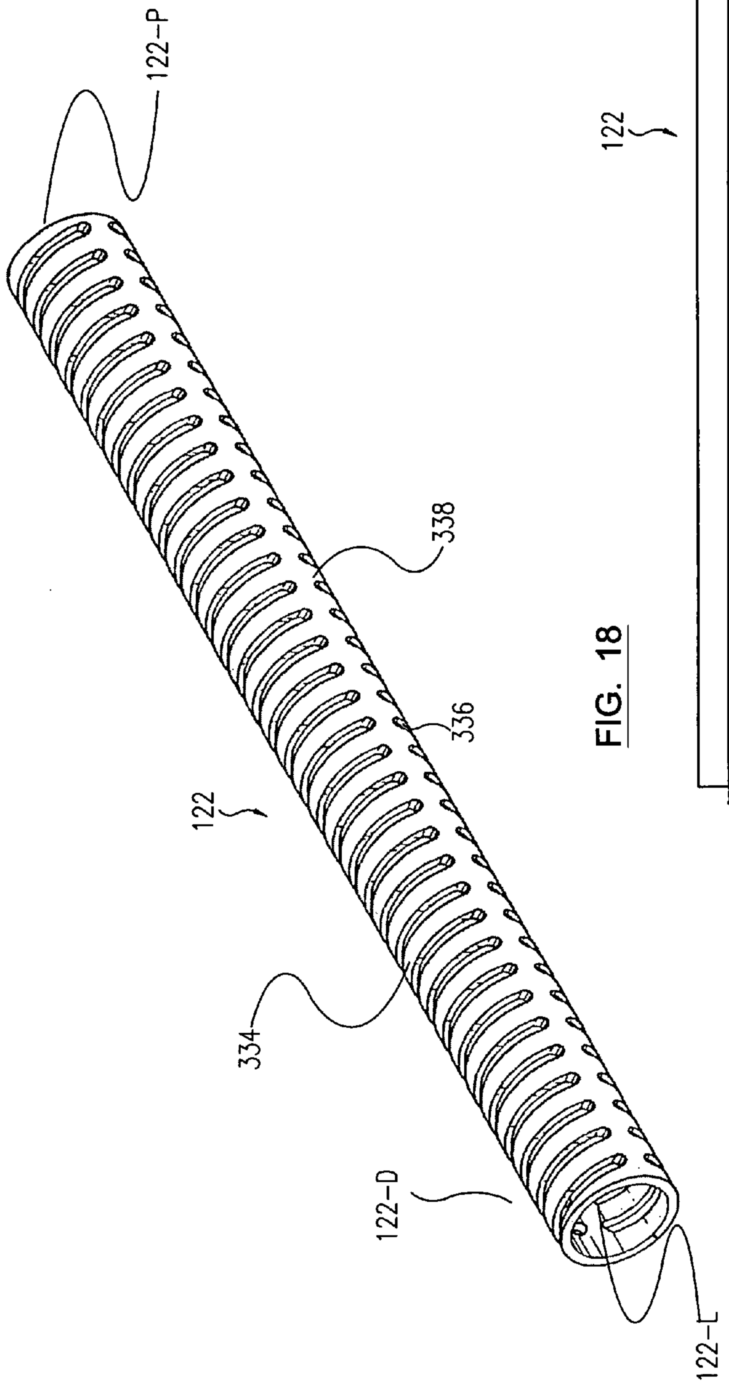

In another embodiment, as illustrated in FIGS. 17-18, the compression cage 122 includes a substantially tubular member 334 with an array of deep notches 336 that are diametrically opposed to each other. The material remaining between the opposing notches 336 functions as struts 338. The struts 338 can be aligned perpendicular to the lumenal longitudinal axis or aligned at a spiral angle (FIGS. 15-19).

Figure 19:
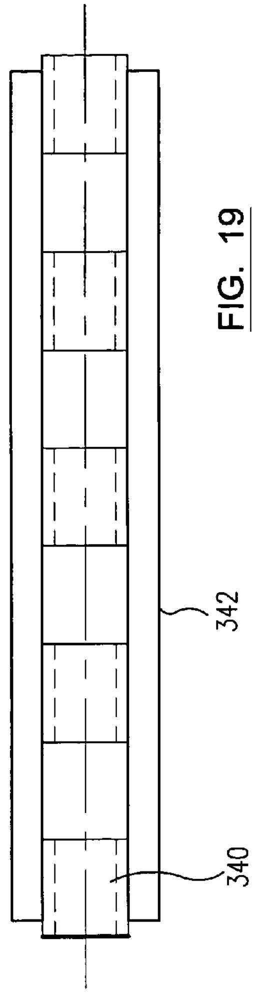

In yet another embodiment, as illustrated in FIG. 19, the compression cage 122 includes a linear array of rings 340 and two substantially longitudinal struts 342 that interconnect the rings 340. The struts 342 are diametrically opposed to each other and are welded, soldered, brazed, adhered, or otherwise attached to each of the rings 340.

The primary function of the struts 328, 332, 338, and 342 is to provide columnar strength to the compression cage 122. When a tensile load is applied to the steering tendon 130 to induce deflection of the catheter distal section 102, the reaction of the load is carried by the struts 328, 332, 338, and 342 within the compression cage 122 and transferred to the catheter proximal section 104. The compression cage 122 deflects laterally most easily in a direction that is perpendicular to the plane in which a pair of opposing struts 328, 332, 338, or 342 are located.

The compression cage 122 maybe attached to the inner surface of the distal catheter shaft 120 by melt-bonding, adhesive, or some equivalent mechanical binding techniques. Alternatively, the compression cage 122 may be combined with the distal catheter jacket 120 into one integral component. Alternatively, the compression cage 122 may reside loosely within the distal catheter shaft 118 provided its distal end and proximal end are connected so as to transfer axial loads through the opposite struts 328, 332, 338, and 342. In one embodiment, the heat source is only applied over the distal portion 122-D and the proximal portion 122-P of the compression cage 122 such that the polymer only melts into these two portions. Thus the compression cage resides loosely in the section between the distal portion 122-D and the proximal portion 122-P.

Figure 20:
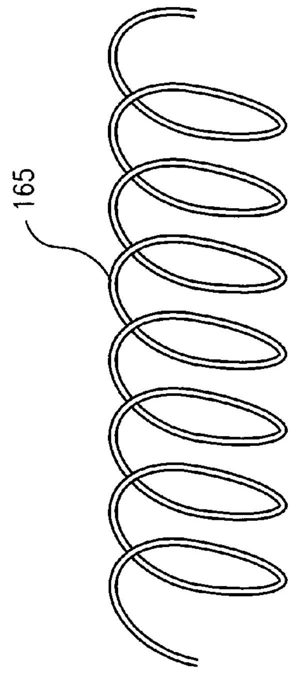
FIG. 20 illustrates a helical coil structure that can resist the compression of the catheter shaft distal section.
Figure 21:
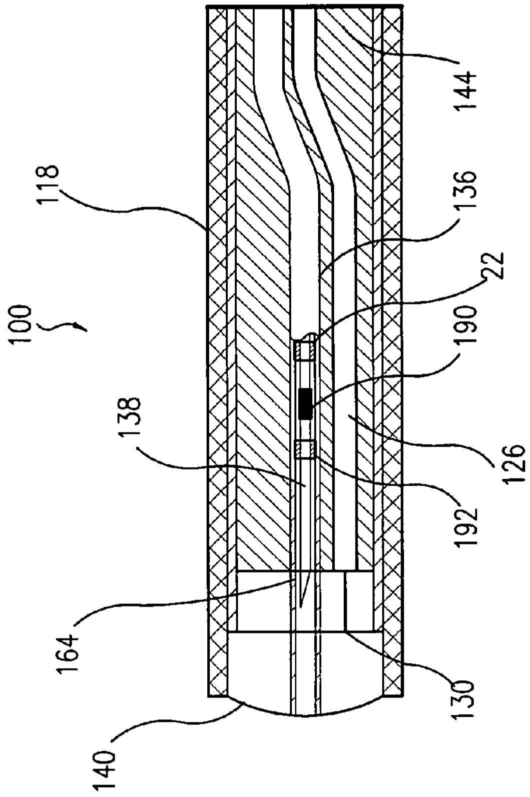
FIG. 21 illustrates an exemplary embodiment of a needle disposed within a catheter assembly wherein the needle includes a interference mechanism that can control the travel distance of the needle.

In an alternative embodiment, the compression cage 122 is replaced with a helical coil structure 165 shown in FIG. 20. The helical coil structure 165 can be made of a resilient material such as stainless steel, Nylon, or Nitinol. The helical coil structure 165 can be a braided mesh made of round wires or ribbons. During the heat fusion process, the heat source is applied to the distal portion and the proximal portion of the helical coil structure 165. The polymer having a low durometer from the distal jacket 120 melts into these two portions. The helical coil structure 165 resides loosely in the section between the distal portion and the proximal portion similar to the case of the compression cage 122. Alternatively, heat can be applied across the entire section of the helical coil structure and the polymer will melt over the entire helical coil structure 165.

After the catheter shaft 101 is formed, a transition section 106 (FIG. 8) is formed near the proximal end of the catheter distal section 102. Several features define the transition section 106. First, the tendon 130 is shifted from the center of the catheter shaft 101 to being off-center at the transition section 106 thus, creating an off-center moment when the tendon 130 is pulled. Second, the distal catheter shaft 118 is made much more flexible compared to the proximal catheter shaft 104 thus, creating a bias for deflection under the tension from the tendon 130. Third, and in some embodiments, in addition to the change in the tendon 130 location, the needle assembly 109 is moved toward the center of the distal catheter shaft118. Fourth, the proximal catheter shaft 112 is transitioned to the distal catheter shaft 118. Fifth, the proximal core shaft 116 is transitioned to the compression cage 122 and distal core shaft 124.

After the catheter shaft 101 is formed, the needle assembly 109 is disposed within the catheter shaft 101 (FIG. 8). It is appreciated that more than one needle assembly (e.g., needle assembly 109) may be disposed within the catheter shaft 101. For example, as illustrated in FIG. 10, needle assemblies 105 and 107 are included along with the needle assembly 109. Each of the needle assemblies, 109, 105, and 107 may include a lubricious or low-friction needle sheath (e.g., made of PTFE or TEFLON) disposed on the outside of the needle assembly to facilitate the movement of the needle assembly within the lumen. Alternatively, each needle assembly may be coated with a lubricious material or be made of a lubricious material to facilitate the movement of the needle assembly within the lumen. Each needle assembly is extendable from the distal end of the catheter shaft 101 to outside of the catheter shaft 101 at the proximal end. Each needle assembly may include a compression compensation mechanism 10 or 11 at their proximal ends as previously described.

At the distal end of the catheter shaft 101, the needle sheath may be glued or otherwise adhered to the distal tip anchor 140. The distal end of the catheter shaft 101 includes an exit opening 97 (FIG. 8) to allow the needle assembly 109 to exit the catheter shaft 101 and reach a target site. In one embodiment, each needle assembly is coupled to an injection port (e.g., connection port 204 shown in FIG. 1). Each needle assembly includes a needle made of a durable material such as metal, stainless steel, Nitinol, polymer, or a combination thereof. The needle can be any conventional needle as is known in the art. The needle typically has a beveled tip or a sharp tip to allow it to enter a target site for treatment.

After the catheter shaft 101 is formed, the tendon 130 is disposed within the catheter shaft 101. The tendon 130 is only inserted into the catheter shaft 101 after all the internal components of the catheter shaft 101 are assembled into the catheter shaft 101. Referring to FIG. 8, the catheter assembly 100 includes a distal tip anchor 140 at the distal end of the distal catheter shaft 118. The distal tip anchor 140 is made with a metallic material such as stainless steel, platinum alloy, brass, or the like, in one embodiment. The distal tip anchor 140 is coupled to the compression cage 122 and the distal catheter shaft 118, for example by, adhesive, welding, soldering, crimping, mechanical interference, etc.

In one embodiment, the distal tip anchor 140 functions as a tendon anchor. The tendon 130 is coupled to the wall of the distal tip anchor 120 by adhesive, welding, soldering, crimping, mechanical interference, or other suitable technique. In one embodiment, after the tendon 130 is coupled to the distal tip anchor 120, the tendon 130 is then inserted into the tendon lumen 126 from the distal end of the distal catheter shaft 118. The tendon 130 is pushed proximally until the tendon 130 reaches the proximal catheter shaft 112 and extends out of the proximal catheter shaft 112.

The tendon 130 is made of metallic wire having a high yield strength and high elastic modulus. Stainless steel or cold worked Nitinol can be used to make the tendon 130 to provide it with such properties. The tendon 130 can have round, rectangular, or other suitable shape cross sections. Alternatively, the tendon 130 can also be made out of a polymeric material such as Kevlar® (Kevlar is a registered trademark of Dupont). The tendon 130 can be made of other suitable materials known in the art that are used for deflectable catheters.

The movement of the tendon 130 and the needles (e.g., needles 123, 125, or 138) is controlled by a catheter handle 200 (see below) attached to the proximal end of the catheter shaft 101. The tendon 130 is coupled to a pull-mechanism (which is included in the catheter handle 200), which has a limited travel distance. When the tendon 130 is pulled, the catheter distal section 102 deflects. The travel distance of the pull-mechanism can be locked at any location and will only move under a manual force.

In some embodiments, the spring components of the compression mechanism 10 or 11 can be replaced by other biasing components or members such as elastic components (e.g., silicon components, rubber bands, and elastomers), air pressure (e.g., air cylinder), and electro magnets. In addition, the spring components can also has different spring configurations such as constant force springs.

In some embodiments, the handle 200 and its enclosed components may be incorporated into a handle that communicates with other shaft 101 lumens (e.g., when the catheter shaft 101 has multiple lumens) to allow access to those lumens and/or to provide functionality to those lumens. For example, pressure monitoring lumens, Optical Coherent Tomography (OCT) lumens, Electrode Cardiogram (ECG) electrode wire lumens, deflection tendon lumens, other needle lumens, etc. . . .

In any of the embodiments previously describe, the catheter shaft of the catheter assembly may include radiopaque markers or have portions of the catheter shaft made out of radio-opaque markers to facilitate in the monitoring and/or locating of the catheter shaft inside a patient. In one embodiment, a radio-opaque powder is mixed into polymers used for all of the outer jackets of the catheter shaft to make the catheter visible under fluoroscope. In other embodiments, a radio-opaque powder is mixed into polymers used for the catheter guide sheath that is used to guide the catheter shaft into the patient's body. Examples of radio-opaque powder include bismuth subcarbonate, also called bismuth oxycarbonate, barium sulfate, and tungsten. The radio-opaque materials typically come in powder form and are used as a radio-opaque salt compounded with other polymer to make radio-opaque polymer.

Figure 22:
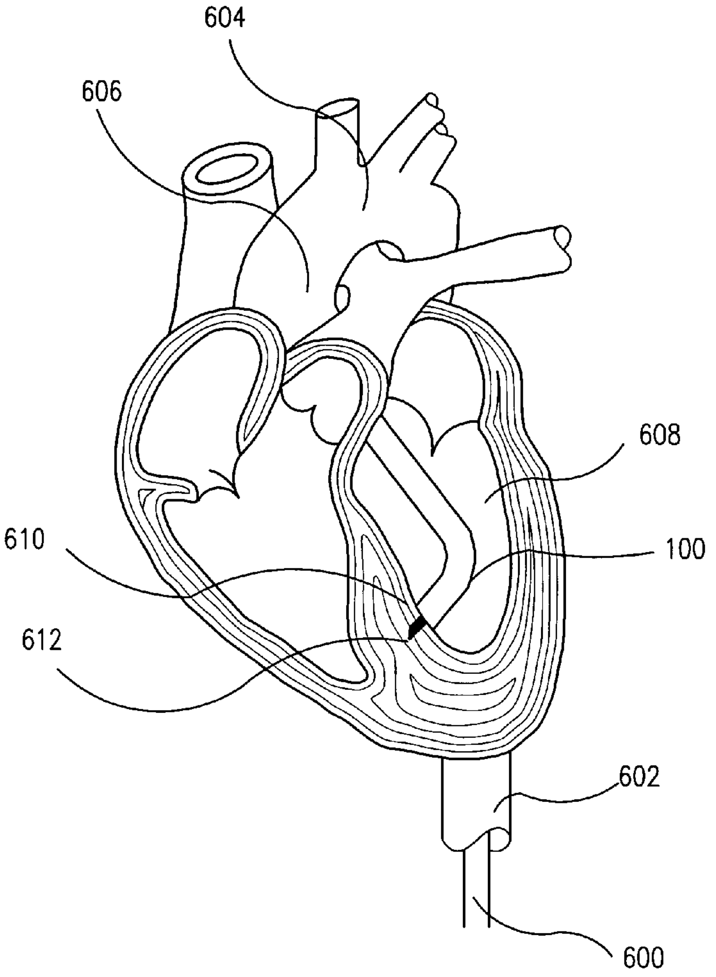
FIG. 22 illustrates an exemplary method of delivering one of the exemplary catheter assemblies of the present invention into the heart.

FIG. 22 illustrates an exemplary procedure that uses the catheter assembly 100 previously described. In one embodiment, a catheter assembly 100 is used to deliver an agent into the left ventricle of a patient. The catheter assembly 100 is inserted into the femoral artery in the groin region (not shown) through an access path created by a percutaneously placed introducer sheath as is well known in the art. The catheter assembly 100 travels into the descending aorta artery 602, over the aortic arch 604, down the ascending aorta 606, across the aortic valve (not shown) and into the left ventricle 608.

Target injection sites (e.g., a target injection site 610) have been determined prior to the delivery procedure. The operator manipulates the catheter assembly 100 to each target 610 location. The manipulation is done by motions of sliding the catheter assembly 100 up and down the ventricle 608 cavity, rotating the catheter assembly 100 to reach different targets in the radial directions (e.g., anterior, lateral, septal wall), and deflecting the catheter distal section to reach the wall. In one embodiment, deflection of the catheter distal section is activated by manipulating the handle 200 as described in the U.S. patent application Ser. No. 10/676,616 previously incorporated and cited. Once the catheter tip is in contact with the target wall, the operator holds the catheter assembly 100 steady, extends the needle 612 of the catheter assembly 100 to the pre-set interference, injects a prescribed dose of bioagent, retracts the needle 612 and moves the catheter assembly 100 to another target location. The contact of the catheter assembly 100 with the ventricular wall can be easily identified. The catheter tip will be seen bouncing with the wall at every contraction cycle and the EKG signal will also change. When the procedure is complete, the catheter is withdrawn from the vasculature.

The needles of the embodiments of the disclosure can be used to deliver a wide range of therapeutic agent or biologic such as cells, drugs, or other fluids. For examples, biological agents such as growth factors (endothelial growth factor (VEFG) and fibroblast growth factors (FGF)), angiogenic agents (angiostatin and endostatin), cells (myogenic cells, bone marrow derived stem cells, endothelial cells, cardiomyocytes), genetic materials (DNA, RNA (virus or other vector based), and iRNA), biochemical agents, small molecule agents, and/or any combination of the above agents, can be delivered using the needles included in the catheter assemblies previously described.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the scope of this invention.

We claim:

1. A deflectable catheter assembly comprising:
- a catheter shaft having a catheter proximal section and a catheter distal section;
- a therapeutic tool disposed within said catheter shaft;
- a compression and extension compensation mechanism coupling to said therapeutic tool to compensate for a length change in said catheter shaft, said compression and extension compensation mechanism including a spring moveably disposed between but not extending beyond a distal stop and a proximal stop, the spring fixedly attached to the distal stop and to the proximal stop to compensate for a compression in length of the catheter shaft by applying a force on the distal stop in the proximal direction, the distal stop and proximal stop being attached to said therapeutic tool;
- a deployment slide moveably disposed proximate to and attached to said spring, said deployment slide between said distal stop and said proximal stop, said deployment slide to deploy said therapeutic tool; and
- a catheter handle coupled to said catheter shaft, said catheter handle to house said compression and extension compensation mechanism.

2. A deflectable catheter assembly as in claim 1 wherein said catheter shaft is deflectable.

3. A deflectable catheter assembly as in claim 1 wherein said compression compensation mechanism coupled to said therapeutic tool at a proximal end of said therapeutic tool.

4. A deflectable catheter assembly as in claim 1 wherein said catheter shaft is deflectable and a tendon is disposed within said catheter shaft, said tendon configured to deflect said catheter distal section when being pulled on.

5. A deflectable catheter assembly as in claim 1 wherein said needle further comprises a stop mechanism that controls extension and retraction distance for said therapeutic tool.

6. A deflectable catheter assembly as in claim 1 wherein the spring compresses or extends to compensate for said length change in said catheter shaft.

7. A deflectable catheter assembly as in claim 1 wherein said catheter shaft includes a lumen for said therapeutic tool to be disposed therethrough.

8. A deflectable catheter assembly as in claim 1 wherein said catheter shaft includes a lumen having a tendon disposed therethrough to deflect said catheter shaft, said lumen is located approximately in the center of said catheter shaft at said catheter proximal section and is located off-center of said catheter shaft at said catheter distal section.

9. A deflectable catheter assembly as in claim 1 wherein said therapeutic tool is located approximately in the center of said catheter shaft at said catheter distal section.

10. A deflectable catheter assembly as in claim 1 further comprises a compression cage disposed in the catheter shaft distal section to prevent compression in said catheter distal section.

11. A deflectable catheter assembly as in claim 1 wherein said therapeutic tool is a needle.

12. A deflectable catheter assembly comprising:
- a catheter shaft having a catheter proximal section and a catheter distal section;
- a therapeutic tool disposed within said catheter shaft;
- a compression and extension compensation mechanism coupling to said therapeutic tool to compensate for a length change in said catheter shaft, said compression and extension compensation mechanism including a first spring and a second spring moveably disposed between but not extending beyond a distal stop and a proximal stop that are attached to said therapeutic tool to compensate for a compression in length of the catheter shaft by applying a force on the distal stop in the proximal direction;
- a deployment slide moveably disposed between and attached to said first spring and said second spring; and
- a catheter handle coupled to said catheter shaft, said catheter handle to house said compression and extension compensation mechanism.

13. A deflectable catheter assembly as in claim 12 wherein said compression mechanism is coupled to said therapeutic tool at a proximal end of said therapeutic tool.

14. A deflectable catheter assembly as in claim 12 wherein said therapeutic tool further comprises a stop mechanism attached to said therapeutic tool at a therapeutic tool distal end to control extension and retraction distance of said therapeutic tool.

15. A deflectable catheter assembly as in claim 12 wherein said first spring is attached at one end to said distal stop and at another end to said deployment slide, and wherein said second spring attached at one end to said deployment slide and at another end to said proximal stop.

16. A deflectable catheter assembly as in claim 12 wherein catheter shaft is deflectable.

17. A deflectable catheter assembly as in claim 16 wherein a tendon disposed within said catheter shaft, said tendon configured to deflect said catheter distal section when being pulled on.

18. A deflectable catheter assembly as in claim 12 wherein said therapeutic tool is a needle.

19. A deflectable catheter assembly as in claim 12 wherein the spring compresses as the catheter shaft is compressed and experiencing said length change to prevent said needle deployment slide from moving proximally to compensate for said length change.

20. A deflectable catheter assembly as in claim 12 wherein said catheter shaft includes a tendon disposed therethrough to deflect said catheter shaft wherein said catheter shaft includes a lumen for each of said tendon and said therapeutic tool to be disposed therethrough.

21. A deflectable catheter assembly as in claim 20 wherein said lumen for said tendon is located approximately in the center of said catheter shaft as said catheter proximal section and is located off-center of said catheter shaft at said catheter distal section.

22. A deflectable catheter assembly as in claim 12 wherein said needle is located approximately in the center of said catheter shaft at said catheter distal section.

23. A deflectable catheter assembly as in claim 12 further comprises a compression cage disposed in the catheter shaft distal section to prevent compression in said catheter distal section.

24. A deflectable catheter assembly as in claim 12 wherein said second spring stabilizes said needle deployment mechanism.

25. A deflectable catheter assembly comprising:

a catheter shaft having a catheter proximal section and a catheter distal section, said catheter distal section being deflectable;

a tendon disposed within said catheter shaft, said tendon configured to deflect said catheter distal section when being pulled on;

a therapeutic tool disposed within said catheter shaft;

a compression and extension compensation mechanism coupling to said therapeutic tool to compensate for a length change in said catheter shaft as said catheter shaft is deflected, said compression and extension compensation mechanism including a spring moveably disposed between but not extending beyond a first proximal stop and a second proximal stop that are fixedly attached to said therapeutic tool, wherein the spring is fixedly attached to the first proximal stop and to the second proximal stop to compensate for a compression in length of the catheter shaft by applying a force on the distal stop in the proximal direction;

a therapeutic tool deployment slide moveably disposed proximate to and fixedly attached to said spring, said deployment slide between said first proximal stop and said second proximal stop; and a catheter handle coupled to said catheter shaft, said catheter handle to house said compression and extension compensation mechanism.

26. A deflectable catheter assembly comprising:

a catheter shaft having a catheter proximal section and a catheter distal section, said catheter distal section being deflectable;

a tendon disposed within said catheter shaft, said tendon configured to deflect said catheter distal section when being pulled on;

a therapeutic tool disposed within said catheter shaft;

a compression and extension compensation mechanism coupling to said therapeutic tool to compensate for a length change in said catheter shaft as said catheter shaft is deflected, said compression and extension compensation mechanism including a first spring and a second spring moveably disposed between but not extending beyond a first proximal stop and a second proximal stop that are fixedly attached to said therapeutic tool to compensate for a compression in length of the catheter shaft by applying a force on the distal stop in the proximal direction;

a therapeutic tool deployment slide moveably disposed between and attached to said first spring and said second spring; and a catheter handle coupled to said catheter shaft, said catheter handle to house said compression and extension compensation mechanism.

27. A deflectable catheter assembly comprising:

a catheter shaft having a catheter proximal section and a catheter distal section;

a therapeutic tool disposed within said catheter shaft;

a compression and extension compensation mechanism coupling to said therapeutic tool to compensate for a length change in said catheter shaft, said compression and extension compensation mechanism including a biasing member moveably disposed between a distal stop and a proximal stop, said biasing member fixedly attached to said distal stop and to said proximal stop to compensate for a compression in length of the catheter shaft by applying a force on the distal stop in the proximal direction, the distal stop and proximal stop being attached to said therapeutic tool;

a deployment slide moveably disposed proximate to and fixedly attached to said biasing member, said deployment slide between said distal stop and said proximal stop, said deployment slide to deploy said therapeutic tool; and a catheter handle coupled to said catheter shaft, said catheter handle to house said compression and extension compensation mechanism.

28. A deflectable catheter assembly as in claim 27 wherein said catheter shaft is deflectable.

29. A deflectable catheter assembly as in claim 27 wherein said catheter shaft is deflectable and a tendon is disposed within said catheter shaft, said tendon configured to deflect said catheter distal section when being pulled on.

30. A deflectable catheter assembly as in claim 27 wherein said therapeutic tool further comprises a stop mechanism that controls extension and retraction distance for said therapeutic tool.

31. A deflectable catheter assembly as in claim 27 wherein the spring compresses or extends to compensate for said length change in said catheter shaft.

32. A deflectable catheter assembly as in claim 27 wherein said catheter shaft includes a lumen for said therapeutic tool to be disposed therethrough.

33. A deflectable catheter assembly as in claim 27 wherein said catheter shaft includes a lumen having a tendon disposed therethrough to deflect said catheter shaft, said lumen is located approximately in the center of said catheter shaft at said catheter proximal section and is located off-center of said catheter shaft at said catheter distal section.

34. A deflectable catheter assembly as in claim 27 wherein said therapeutic tool is located approximately in the center of said catheter shaft at said catheter distal section.

35. A deflectable catheter assembly as in claim 27 further comprises a compression cage disposed in the catheter shaft distal section to prevent compression in said catheter distal section.

36. A deflectable catheter assembly as in claim 27 wherein said therapeutic tool is a needle.

37. A deflectable catheter assembly as in claim 27 wherein said biasing member is any one of an elastic component, a silicon component, a rubber band, an elastomer, air pressure, air cylinder, and an electro magnet, a spring component and a constant force spring.

38. A deflectable catheter assembly as in claim, wherein the spring is attached to the distal stop.

39. A deflectable catheter assembly as in claim 38 wherein the handle further comprises a recessed slot having a proximal recess slot portion and a distal recess slot portion at which the slide can be locked into position.

40. A deflectable catheter assembly as in claim 12 wherein the first spring is attached to the distal stop, and the second spring is attached to the proximal stop.

41. A deflectable catheter assembly as in claim 40 wherein the handle further comprises a recessed slot having a proximal recess slot portion and a distal recess slot portion at which the slide can be locked into position.

42. The deflectable catheter assembly as in claim 38 further comprising a lever extending through and having a portion disposed external to the recessed slot, the lever slidably constrained within the recessed slot.

43. The deflectable catheter assembly as in claim 41 further comprising a lever extending through and having a portion disposed external to the recessed slot, the lever slidably constrained within the recessed slot.

44. The deflectable catheter assembly as in claim 1, wherein the spring causes the force by pulling on the distal stop and the proximal stop.

45. The deflectable catheter assembly as in claim 44, wherein the force on the distal stop in the proximal direction results in a net force on the needle in the proximal direction causing the needle to be moved in the proximal direction.

46. The deflectable catheter assembly as in claim 1, wherein the spring is fixedly attached to the distal stop and to the proximal stop to compensate for movement of the deployment slide in the proximal direction by pulling on the distal stop in the proximal direction.

* * * * *